US011885822B2

(12) United States Patent
Collins et al.

(10) Patent No.: US 11,885,822 B2
(45) Date of Patent: Jan. 30, 2024

(54) APPARATUSES FOR REACTION SCREENING AND OPTIMIZATION, AND METHODS THEREOF

(71) Applicant: SRI International, Menlo Park, CA (US)

(72) Inventors: Nathan Collins, San Mateo, CA (US); Jeremiah Malerich, San Jose, CA (US); Jason D. White, San Jose, CA (US); Kevin Luebke, Staunton, VA (US); Kristina Rucker, Menlo Park, CA (US); Brian McCoy, San Jose, CA (US)

(73) Assignee: SRI International, Menlo Park, CA (US)

( * ) Notice: Subject to any disclaimer, the term of this patent is extended or adjusted under 35 U.S.C. 154(b) by 527 days.

(21) Appl. No.: 16/626,495

(22) PCT Filed: Jun. 29, 2018

(86) PCT No.: PCT/US2018/040431
§ 371 (c)(1),
(2) Date: Dec. 24, 2019

(87) PCT Pub. No.: WO2019/006391
PCT Pub. Date: Jan. 3, 2019

(65) Prior Publication Data
US 2020/0225251 A1 Jul. 16, 2020

Related U.S. Application Data

(60) Provisional application No. 62/527,365, filed on Jun. 30, 2017.

(51) Int. Cl.
*G01N 35/10* (2006.01)
*G01N 35/00* (2006.01)
(Continued)

(52) U.S. Cl.
CPC .... *G01N 35/00613* (2013.01); *B01J 19/0046* (2013.01); *G01N 35/00871* (2013.01);
(Continued)

(58) Field of Classification Search
None
See application file for complete search history.

(56) References Cited

U.S. PATENT DOCUMENTS 4,928,015 A * 5/1990 Butler ............... G01J 3/453
250/339.08
5,463,564 A * 10/1995 Agrafiotis ............ C07K 1/047
260/1
(Continued)

FOREIGN PATENT DOCUMENTS

CN 102656462 A 9/2012
JP H10-132828 A 5/1998
(Continued)

OTHER PUBLICATIONS

Schneider, G. Automating drug discovery. Nat Rev Drug Discov 17, 97-113 (2018).
(Continued)

*Primary Examiner* — P. Kathryn Wright
(74) *Attorney, Agent, or Firm* — Dicke, Billig & Czaja, PLLC

(57) ABSTRACT

Embodiments in accordance with the present disclosure are directed to apparatuses used for reaction screening and optimization purposes. An example apparatus includes a plurality of reaction vessels, a dispensing subsystem, at least one reactor module, an analysis subsystem, an automation subsystem, and control circuitry. The dispensing subsystem delivers reagents to the plurality of reaction vessels for a plurality of reaction mixtures having varied reaction conditions. The at least one reactor module drives a plurality of
(Continued)

reactions within the plurality of reaction vessels. The analysis subsystem analyzes compositions contained in the plurality of reaction vessels. The automation subsystem selectively moves the plurality of reaction vessels from a location proximal to the dispensing subsystem to the at least one reactor module based on experimental design parameters. And, the control circuitry identifies optimum reaction conditions for a target end product based on the analysis.

20 Claims, 22 Drawing Sheets

(51) Int. Cl.
| | |
|---|---|
| G01N 35/04 | (2006.01) |
| B01J 19/00 | (2006.01) |
| G16C 20/10 | (2019.01) |
| G16C 20/70 | (2019.01) |
| G16C 10/00 | (2019.01) |

(52) U.S. Cl.
CPC ......... *G01N 35/04* (2013.01); *G01N 35/1002* (2013.01); *G16C 10/00* (2019.02); *G16C 20/10* (2019.02); *G16C 20/70* (2019.02); *B01J 2219/00344* (2013.01); *B01J 2219/00351* (2013.01); *B01J 2219/00495* (2013.01); *B01J 2219/00689* (2013.01); *B01J 2219/00693* (2013.01); *B01J 2219/00695* (2013.01); *B01J 2219/00698* (2013.01); *G01N 2035/00346* (2013.01); *G01N 2035/0403* (2013.01); *G01N 2035/0496* (2013.01)

(56) References Cited

U.S. PATENT DOCUMENTS

| | | | |
|---|---|---|---|
| 5,959,297 A | 9/1999 | Weinberg et al. | |
| 6,044,212 A | 3/2000 | Flavin et al. | |
| 6,086,831 A | 7/2000 | Harness et al. | |
| 6,421,612 B1 * | 7/2002 | Agrafiotis | G06K 9/6251 |
| | | | 702/19 |
| 6,440,722 B1 | 8/2002 | Knapp et al. | |
| 6,508,984 B1 | 1/2003 | Turner et al. | |
| 6,663,832 B2 | 12/2003 | Lebl et al. | |
| 6,673,316 B1 * | 1/2004 | Okamoto | B01J 19/0046 |
| | | | 422/65 |
| 6,701,774 B2 | 3/2004 | Srinivasan et al. | |
| 6,727,096 B1 | 4/2004 | Wang et al. | |
| 6,730,517 B1 * | 5/2004 | Koster | G01N 35/0099 |
| | | | 422/65 |
| 7,288,229 B2 | 10/2007 | Turner | |
| 7,390,458 B2 | 6/2008 | Burow et al. | |
| 7,998,436 B2 | 8/2011 | Pollack et al. | |
| 2002/0001538 A1 | 1/2002 | Hajduk et al. | |
| 2002/0042140 A1 | 4/2002 | Hagemeyer et al. | |
| 2002/0090728 A1 | 7/2002 | Shair et al. | |
| 2002/0120432 A1 | 8/2002 | Ager et al. | |
| 2002/0143476 A1 * | 10/2002 | Agrafiotis | G06N 3/02 |
| | | | 702/32 |
| 2003/0086829 A1 | 5/2003 | Livesay et al. | |
| 2003/0157721 A1 | 8/2003 | Turner et al. | |
| 2003/0220716 A1 * | 11/2003 | Mydlowec | G16C 20/10 |
| | | | 702/27 |
| 2007/0021929 A1 * | 1/2007 | Lemmo | G01N 35/0092 |
| | | | 702/22 |
| 2009/0137048 A1 | 5/2009 | Yamazaki et al. | |
| 2013/0266484 A1 | 10/2013 | Kamihara et al. | |
| 2013/0295597 A1 | 11/2013 | DeWitte et al. | |
| 2014/0323330 A1 | 10/2014 | Bergo | |
| 2016/0320381 A1 * | 11/2016 | Holmes | G01N 35/026 |
| 2017/0098534 A1 | 4/2017 | Brown et al. | |
| 2020/0316552 A1 * | 10/2020 | Lim | B01J 19/0006 |

FOREIGN PATENT DOCUMENTS

| | | | | |
|---|---|---|---|---|
| WO | 2001066245 A2 | 9/2001 | | |
| WO | WO-03083609 A2 * | 10/2003 | ........... | G06F 19/702 |
| WO | WO-2007148130 A1 * | 12/2007 | ........... | G06F 19/706 |

OTHER PUBLICATIONS

Cole, K. P., Groh, J. M., Johnson, M. D., Burcham, C. L., Campbell, B. M., Diseroad, W. D., . . . Gowran, O. (2017). Kilogram-scale prexasertib monolactate monohydrate synthesis under continuous-flow CGMP conditions. Science, 356 (6343), 1144-1150.

Aaron B. Beeler, Shun Su, Chris A. Singleton, and John A. Porco, Jr. Discovery of Chemical Reactions through Multidimensional Screening. Journal of the American Chemical Society 2007 129 (5), 1413-1419.

Alexander Buitrago Santanilla, Erik L. Regalado, Tony Pereira, Michael Shevlin, Kevin Bateman, Louis-Charles Campeau, Jonathan Schneeweis, Simon Berritt, Zhi-Cai Shi, Philippe Nantermet, Yong Liu, Roy Helmy, Christopher J. Welch, Petr Vachal, Ian W. Davies, Tim Cernak, Spencer D. Dreher. Nanomole-scale high-throughput chemistry for the synthesis of complex molecules Science Jan. 2, 2015 : 49-53.

Cody, R. Direct Analysis in Real Time (DART) Mass Spectrometry. JEOL News. 2001, vol. 36E, No. 1.

Gross, JH. Direct Analysis in Real Time—A Critical Review on DART-MS. Anal Bioanal Chem. 2014, vol. 406, pp. 63-80.

Fleischer, H, et al. Application of a Dual-Arm Robot in Complex Sample Preparation and Measurement Processes, Journal of Laboratory Automation, 2016, vol. 21, No. 5, p. 671-681.

Extended European Search report for related European Patent Application No. 18823357.1 dated Mar. 18, 2021.

First Chinese Office Action for related Chinese Patent Application No. 201880056935.8 dated May 8, 2021.

Japanese Notification of Reasons for Refusal dated Mar. 22, 2022 for corresponding Japanese patent application 2019-572559.

Japanese Notification of Reasons for Refusal dated Mar. 22, 2022 for corresponding Japanese patent application 2019-572559. (English translation).

* cited by examiner

| ITEM NO. | PART NUMBER | DESCRIPTION | break apart/QTY. |
|---|---|---|---|
| 1 | Tool | | 1 |
| 2 | 20 mL chamber reaction | | 1 |
| 3 | Tool Cap | | 1 |
| 4 | Wedge | | 1 |

APPARATUSES FOR REACTION SCREENING AND OPTIMIZATION, AND METHODS THEREOF

FEDERALLY-SPONSORED RESEARCH AND DEVELOPMENT

This invention was made with Government support under contract no. W91 INF-16-C-0051 awarded by the Defense Advanced Research Projects Agency. The Government has certain rights in this invention.

OVERVIEW

Organic compounds, such as pharmaceutical compounds, can be prepared by synthetic routes involving multiple chemical steps. Many plausible strategies can be designed to prepare a target compound through the use of creative chemists and computation systems with access to chemical data. Validating an optimal synthetic strategy, including reaction pathways for reaching the desired compound, can be time consuming. For example, finding the optimal synthetic strategy can take years of research which may not include an exhaustive search of a total list of potential synthetic approaches due to the vast combination of different pathways. Establishing synthetic routes adds to the increasing cost of developing new complex organic compounds, such as pharmaceuticals, chemical probes, diagnostics, high energy material, and polymers. As an example, it is estimated that pharmaceutical companies spend between five to twenty years and budgets of millions to hundreds of millions of dollars to find economically viable syntheses of pharmaceutical compounds, and then continue to strive to optimize the process to reduce production costs.

SUMMARY OF THE INVENTION

The present invention is directed to overcoming the above-mentioned challenges and others related to reaction screening and optimization of reaction pathways for a target end product (e.g., a compound) for particular purposes.

Various aspects of the present disclosure are directed to apparatuses and methods thereof that can be used to optimize a reaction for reaching a target end product for more than one objective and/or more than one varied reaction condition at a time.

In various specific embodiments, an apparatus includes a plurality of reaction vessels, a dispensing subsystem, at least one reactor module, an automation subsystem, and control circuitry. The reaction vessels can be provided or contained within a substrate. The dispensing subsystem delivers reagents to the plurality of reaction vessels for a plurality of reaction mixtures having varied reaction conditions. The at least one reactor module drives a plurality of reactions within the plurality of reaction vessels and in accordance with the varied reaction conditions. For example, the at least one reactor module includes an energy emitter that provides an energy output toward the plurality of reaction vessels and thereby drive the plurality of reactions. The varied reaction conditions can include temperature. times, concentrations of reagents, reagents, among other variations. The analysis subsystem analyzes compositions of reaction mixtures (e.g., reactants, side products, end products, and byproducts) contained in the plurality of reaction vessels after the reactions have begun and, optionally, at any time during a set of reaction times. The analysis can be performed at a speed on an order of and/or up to one reaction per second (or more). The automation subsystem selectively moves the plurality of reaction vessels from a location proximal to the dispensing subsystem to the at least one reactor module based on experimental design parameters (e.g., that define the varied reaction conditions). The control circuit provides the experimental design parameters to the dispensing subsystem and the automation subsystem for feedback control of the plurality of reactions within a threshold period of time and to identify optimum reaction conditions for a target end product based on the analysis of the compositions received from the analysis subsystem.

In more specific embodiments, the feedback control provided by the control circuit adjusting the varied reaction conditions for a plurality of additional reactions based upon comparing previous reaction results with optimal reaction product yields stored in the analysis subsystem. For example, the control circuit provides the adjusted varied reaction conditions as revised experimental design parameters to the dispensing subsystem and the automation subsystem, which can be instantaneous or near-instantaneous.

The plurality of reaction mixtures can be exposed to the same or different additional reaction conditions (e.g., the same temperature, same exposure time, or various combinations of temperatures and/or exposure times). As a specific example, the varied reaction conditions can include exposure to different temperatures for different periods of time. The at least one reactor module can include a plurality of reactor modules or one reaction module with different zones that drive the plurality of reactions in parallel and at a plurality of different temperatures, and each of the reactor modules includes a thermal energy emitter that provides thermal energy toward at least a portion of the plurality of reaction mixtures. In such example embodiments, the reaction vessels are independently selectable from one another, and the automation subsystem selectively moves a first of the plurality of reaction vessels to a first location associated with the at least one reactor module, selectively moves a second of the plurality of reaction vessels to a second location associated with the at least one reactor module, and moves each of the first and second of the plurality of reaction vessels to a location proximal to the analysis subsystem upon completion of the respective reactions. In other embodiments, the reaction vessels or a subset can be located on a substrate and the substrate (as a whole) is moved to a reactor module and exposed to a temperature.

The automation subsystem can move the reaction vessels, reaction mixtures, substrates or other components (e.g., caps) to various locations associated with the apparatus. The reaction mixtures can be moved from a location proximal to the dispensing subsystem to the at least one reactor module for driving the reactions. The automation subsystem can additionally move the reaction mixtures (all or select ones) back to the dispensing subsystem for adding additional reagents and/or to the analysis subsystem. For example, the automation subsystem moves the reaction mixtures from the at least one reactor module to a location proximal to the analysis subsystem, and the analysis subsystem emits an analysis beam toward each of the plurality of reaction vessels that is approximately parallel to a top portion of the reaction vessels. In more specific embodiments, the control circuitry and the automation subsystem seal each of the plurality of reaction vessels prior to the plurality of reactions being driven within the reaction vessels, and unseal each of the plurality of reaction vessels mid-reaction to introduce other reagents to sample the reaction mixture, or prior to the analysis of the compositions of reaction mixtures (e.g., reactants, side products, end products, and byproducts).

Furthermore, the apparatus can optionally include one or more distribution chambers used for distributing the reaction vessels and the caps to the automation subsystem.

The dispensing system can include an inkjet printer, a liquid dispenser, and a combination thereof. For example, the inkjet printer can have a printer head, such as an 8-channel printer head, 9-channel printer head or 96-channel printer head, used to disperse the reagents to the reaction vessels.

The analysis subsystem can include a liquid chromatography-mass spectrometer (LC-MS), a real time (DART)-mass spectrometer (MS), a spectroscopic imager, and a combination thereof. For example, a component of the DART-MS provides a beam of gas directed toward each reaction mixture sequentially and carries a sampling of each reaction mixture to another component of the DART-MS. The beam can be provided toward the top of the reaction vessels, such as at an angle of 0-45 degrees relative to normal. The beam can result or cause a detectable audio frequency which can be used to verify analysis is being conducted. In some specific embodiments, the apparatus further includes sensor circuitry that provides a detectable audio frequency signal to the control circuitry in response to the analysis beam sampling of each reaction mixture, and the control circuitry compares the detected audio frequency signal to a threshold audio frequency and therefrom verifies whether analysis is occurring. In other embodiments, the apparatus can include imaging circuitry used to capture a visual image of the (e.g., each) reaction vessels and from the visual image, verifies whether analysis is occurring.

Other related and specific embodiments of the present disclosure are directed to an apparatus that includes a plurality of reaction vessels that are individually selectable and separable, at least one reactor module, an analysis subsystem, an automation subsystem, control circuitry. The plurality of reaction vessels includes reagents contained therein according to experimental design parameters for a plurality of reaction mixtures having varied reaction conditions. The at least one reactor module drives a plurality of reactions within the plurality of reaction vessels in accordance with the varied reaction conditions, the reaction varied conditions including exposure to different temperatures for different periods of time. The analysis subsystem analyzes compositions of reaction mixtures (e.g., reactants, side products, end products, and byproducts) contained within the plurality of reaction vessels after the reactions have begun and at any time during a set of reaction times by providing an analysis beam selectively toward the plurality of reaction mixtures and analyzing results therefrom at a speed on an order of one reaction per second, such as a speed of up to one reaction per second or more. The automation subsystem seals the plurality of reaction vessels, selectively moves the plurality of reaction vessels to and from the at least one reactor module for the different periods of time based on the experimental design parameters, and unseals the plurality of reaction vessels and selectively moves the reaction mixtures proximal to the analysis subsystem after reaction. The control circuitry provides the experimental design parameters to the automation subsystem for controlling the reactions within the plurality of reaction vessels and to identify optimum reaction conditions for a target end product based on the analysis of the compositions received from the analysis subsystem.

The automation circuitry, in specific aspects, includes a movable arm and a distribution chamber. The distribution chamber contains a plurality of caps for the plurality of reaction vessels. The movable arm and distribution chamber distribute the plurality of caps for the plurality of reaction vessels and seal the plurality of reaction vessels using the distributed caps. As further described herein, the movable arm can include head assembly used to select the reaction vessels and an interconnected set of links and power joints that can be used to move the head assembly.

In specific embodiments, the above-described apparatus can further include a dispensing subsystem that delivers reagents to the plurality of reaction vessels for the plurality of reaction mixtures having the varied reaction conditions. The automation subsystem can selectively move the plurality of reaction vessels from a location proximal to the dispensing subsystem to the at least one reactor module. And, the control circuitry provides the experimental design parameters to the dispensing subsystem, the experimental design parameters including identification of reagents, concentration of reagents for each of the plurality of reaction vessels, and the other varied reaction conditions.

Specific embodiments in accordance with the present disclosure are directed to a method of using the above-described apparatuses. The method can include providing a plurality of experimental design parameters, via control circuitry, to a dispensing subsystem and an automation subsystem for controlling a plurality of reactions within a plurality of reaction vessels. The method further includes delivering different amounts of reagents to respective reaction vessels of the plurality of reaction vessels by the dispensing subsystem and according to the experimental design parameters. The subsystem can selectively move the plurality of reaction vessels from a location proximal to the dispensing subsystem to the at least one reactor module, where the plurality of reactions are driven. For example, the plurality of reactions is driven within the plurality of reaction vessels in accordance with varied reaction conditions, including exposure to different temperatures and different periods of time, as defined by the experimental design parameters and by the at least one reactor module. The method further includes analyzing compositions contained within the plurality of reaction vessels at a speed on an order of (e.g., up to or more than) one reaction per second and identifying optimum reaction conditions for a target end product based on the analysis.

As described above, in some aspects, the method further includes selectively moving the plurality of reaction vessels to a location proximal to an analysis subsystem responsive to the plurality of reactions being driven to completion. The analysis subsystem provides a beam of gas that can be moveably directed toward each of the plurality of reaction vessels. The beam of gas can be directed at an angle that is approximately parallel to a top portion of the plurality of reaction vessels and the gas beam carries a sampling of the reaction mixture to an analysis subsystem for analyzing the compositions contained in the reaction vessels based on ions generated therefrom.

In various related aspects, the method includes delivering different amounts of reagents by providing a plurality of reaction mixtures having different concentrations of reagents to different reaction vessels of the plurality of reaction vessels according to the experimental design parameters. The reagents can be provided at the same time or at different times throughout the experiment.

Identifying the optimum reaction conditions for the target end product can further include identifying optimized experimental design parameters selected from the group consisting of: reagents, concentration of reagents, temperature, time, stoichiometry, and a combination thereof. The optimum reaction conditions can be further optimized by providing feedback. For example, the method can further include providing, based on the analysis of compositions contained within the reaction vessel, adjusted varied reaction conditions for a plurality of additional reactions designed to reach revised optimum reaction conditions for the target end product, and providing the adjusted varied reaction conditions as revised experimental design parameters to the dispensing subsystem and the automation subsystem. Using the revised experimental design parameters, the apparatus can run an additional test and further optimize the reaction conditions from an analysis of compositions therefrom.

Embodiments in accordance with the present disclosure include all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which.

Figure 1:
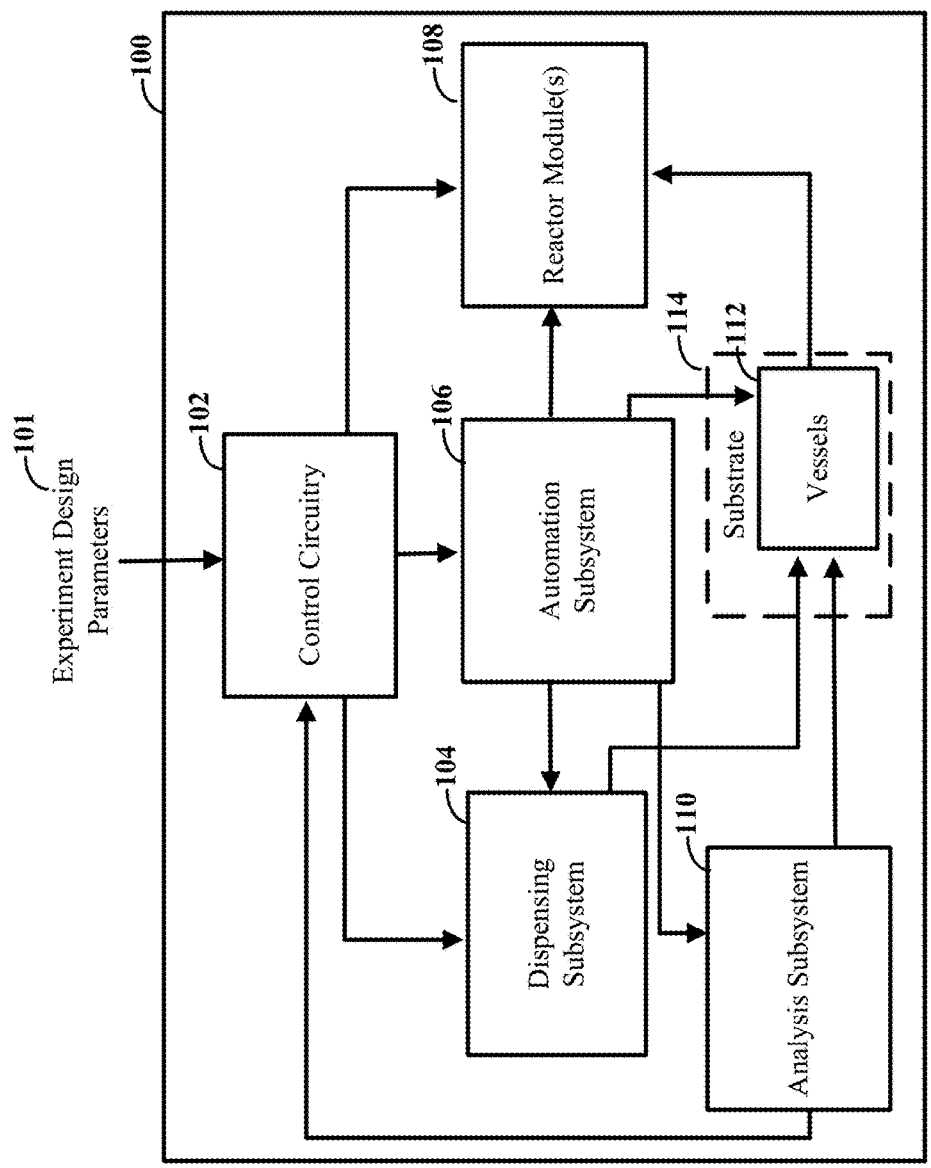
FIG. 1 illustrates an example of apparatus that performs reaction screening and optimization, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to variety of apparatuses used for performing reaction screening and optimization for reaction conditions of a target end product. In certain implementations, the apparatus is used to deliver reaction mixtures with spatial, temporal, and quantitative control, reaction condition control, and inline analysis. In some specific implementations, the above-described control is used together with machine learning reaction design based on feedback of results from previous reactions and can be used to analyze compositions at a speed on an order of one reaction per second. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique of performing reaction screening and optimization for a target end product, and which identifies a reaction pathway that utilizes specific reaction conditions. A reaction can have multiple inputs (e.g., reaction conditions) and provides a desired output (e.g., an end product that achieves an objective). Example reaction conditions include temperature, reagent concentrations or stoichiometry, pH, time, among other conditions. Outputs includes a target end product that exhibits or is formed by a particular objective, such as particular product yield, selectivity, purity, time and/or cost, among other objectives. As may be appreciated, the reaction conditions impact the output. Reaction optimization refers to the process of identifying a set of reaction conditions that achieves at least one objective in an optimal manner. Embodiments in accordance with the present disclosure are directed toward optimizing a reaction for reaching a target end product for more than one objective and/or more than one varied reaction condition at a time.

Identifying an optimum synthetic strategy for a target end product, such as a complex organic compound, can often take years of research and may not include an exhaustive search for the total list of approaches. In many instances, reactions are screened by making small volume reaction mixtures and monitoring the reaction by removing aliquots for offline analysis. The time for optimizing reaction screening is impacted by: the time for design and selection of reactions; total reaction time; the time to order, assemble, and prepare reagents; the time and effort for preparing the reaction mixtures, and, the time for analyzing compositions of the reactions. For example, ordering, assembly, weighing, and preparing of reagents can take weeks of lead time. The manual preparation of transferring, weighing, dissolving, and delivering reagents to reaction vessels followed by reacting, analyzing, and interpreting the results is a major undertaking that limits the number of reactions a chemist can conduct. By a manual process, an efficient chemist can often run one to ten reactions a day. Embodiments in accordance with the present application are directed to apparatuses that include liquid handling robotics and on-line analytics through the use computer aided design of predicted chemical routes, which involves acquiring and preparing tens to hundreds of reagents and solvents in various ratios. An example apparatus can include a dispensing subsystem that dispenses reagent combinations to create reaction mixtures and reaction vessels for individual or batched reactions that allow for continuous processing of reactions through the apparatus (or alternatively recalculated through the apparatus for multi-step synthesis or functional screening). The apparatus further includes at least one reactor module for controlling reaction conditions, an in-line analyzer subsystem for analyzing the compositions (of the reaction mixtures) contained within the reaction vessels, and an automation subsystem that controls movement of the reaction mixtures through the reaction and analysis. In various specific embodiments, control circuitry is used to provide design of experiment (DOE) information, such as varied reaction conditions for a plurality of reaction mixtures to the different components of the apparatus. The control circuitry can interpret analysis results and optimize reagents and other reaction conditions in real time.

As described above, an example apparatus in accordance with various embodiments includes control circuitry, a dispensing subsystem, an automation subsystem, at least one reactor module, an analysis subsystem, and a plurality of vessels which can optionally be arranged on a substrate such as a plate. The dispensing subsystem delivers reagents to the plurality of reaction vessels for a plurality of reaction mixtures having varied reaction conditions. The at least one reactor module drives a plurality of reactions within the plurality of reaction vessels and in accordance with the varied reaction conditions. The reactor module includes an energy emitter (e.g., thermal energy tool/radiator) that provides an energy output (e.g., heat) toward the plurality of reaction vessels and thereby drives the plurality of reactions, such as a heater, an oven, a source of microwaves or light. The varied reaction conditions, in specific embodiments, can include temperature, time, concentrations of reagents, and reagents, among other variations. The analysis subsystem analyzes compositions contained in the plurality of reaction vessels after the reactions have begun and, optionally, at any time during a set of reaction times. The analysis can be performed at a speed on an order of one reaction per second, such as a speed up to one reaction per second or more. The automation subsystem selectively moves the plurality of reaction vessels from a location proximal to the dispensing subsystem to the at least one reactor module based on experimental design parameters which include the varied reaction conditions. The control circuit provides the experimental design parameters to the dispensing subsystem and the automation subsystem for feedback control of the plurality of reactions within a threshold period of time and to identify optimum reaction conditions for a target end product based on the analysis of the compositions received from the analysis subsystem.

In specific embodiments, the dispensing subsystem can include an inkjet printer and/or other liquid dispensers. An inkjet printer can deliver reagents in a controlled manner. More specifically, with an inkjet printer, volumes delivered can be small (e.g., pico liters to microliters) and accurate, which allows for optimization of chemistry with minimal amounts of reagents and solvents. Additionally, delivery rates per reagent are in the milliseconds, facilitating rapid reagent combinations to be tested. In various embodiments, the printer heads for the inkjet printer can be disposable, single use printer heads that can be used to print reagents with a range of viscosities. However, embodiments are not limited to inkjet printers and can include the use of liquid dispensers, as further described herein.

Similarly, different types of analyzer subsystems can be used. For example, the analyzer subsystem can include a liquid chromatography-mass spectrometer (LC-MS), a real time (DART)-mass spectrometer (MS), a spectroscopic imager, among other types of analyzers. A MS provides rapid reaction characterization, but other spectroscopic and analytical systems can be employed.

The plurality of reaction mixtures can be exposed to the same temperature and/or for the same time or to various combinations of temperatures and time (e.g., same temperature for different periods of time, to the same temperature for the same period of time, to different temperatures for the same period of time, and/or to different temperatures for different periods of time). In specific embodiments, the varied reaction conditions include exposure to different temperatures for different periods of time, and the reaction vessels are independently selectable from one another. In such example embodiments, the automation subsystem selectively moves a first of the plurality of reaction vessels to a first location associated with the at least one reactor module, selectively moves a second of the plurality of reaction vessels to a second location associated with the at least one reactor module, and moves each of the first and second of the plurality of reaction vessels to a location proximal to the analysis subsystem upon completion of the respective reactions. The at least one reactor module can include a plurality of reactor modules or zones that drive the plurality of reactions in parallel and at a plurality of different temperatures, and each of the reactor modules includes an energy emitter, such as a thermal energy emitter that provides thermal energy toward at least a portion of the plurality of reaction mixtures. In other embodiments, the reaction vessels or a subset can be located on a substrate and the substrate (as a whole) is moved to a reactor module and exposed to a temperature.

The automation subsystem can move the reaction vessels, reaction mixtures, substrates or other components (e.g., caps) to various locations associated with the apparatus. For example, the automation subsystem can move the reaction mixtures from a location proximal to the dispensing subsystem to the at least one reactor module for driving the reactions or at any point during the reactions. The automation subsystem can additionally move the reaction mixtures (all or select ones) back to the dispensing subsystem for adding additional reagents and/or to the analysis subsystem for analysis. In a specific embodiment, the automation subsystem moves the reaction mixtures from the at least one reactor module to a location proximal to the analysis subsystem, and the analysis subsystem emits an analysis beam toward each of the plurality of reaction vessels that is approximately parallel to a top portion of the reaction vessels where the beam is able to blow a sampling of the reaction mixture to a detector portion of the analysis subsystem. In more specific embodiments, the control circuitry and the automation subsystem seal each of the plurality of reaction vessels prior to the plurality of reactions being driven within the reaction vessels, and unseal each of the plurality of reaction vessels mid-reaction to introduce other reagents, to sample the reaction mixture, or prior to the analysis of the compositions. Furthermore, the apparatus can optionally include one or more distribution chambers used for distributing the reaction vessels and the caps to the automation subsystem.

The automation circuitry, in specific embodiments, includes a movable arm and a distribution chamber. The distribution chamber contains a plurality of caps for the plurality of reaction vessels. The movable arm and distribution chamber distribute the plurality of caps for the plurality of reaction vessels and seal the plurality of reaction vessels using the distributed caps. As further described herein, the movable arm can include head assembly used to select the reaction vessels and an interconnected set of links and power joints that can be used to move the head assembly, although embodiments are not so limited.

In other related and specific embodiments, an apparatus includes a plurality of reaction vessels that are individually selectable and separable, at least one reactor module, an analysis subsystem, an automation subsystem, and control circuitry. The plurality of reaction vessels include reagents contained therein according to experimental design parameters for a plurality of reaction mixtures having varied reaction conditions. The at least one reactor module drives a plurality of reactions within the plurality of reaction vessels in accordance with the varied reaction conditions. The analysis subsystem analyzes compositions (e.g., the formation of reaction intermediates or end products of the reaction mixtures) contained within the plurality of reaction vessels after the reactions have begun and at any time during a set of reaction times by providing an analysis beam selectively toward the plurality of reaction mixtures and analyzing results therefrom at a speed on an order of one reaction per second. The automation subsystem seals the plurality of reaction vessels, selectively moves the plurality of reaction vessels to and from the at least one reactor module for the different periods of time based on the experimental design parameters, and unseals the plurality of reaction vessels and selectively moves the reaction mixtures proximal to the analysis subsystem. The control circuitry provides the experimental design parameters to the automation subsystem for controlling the reactions within the plurality of reaction vessels and to identify optimum reaction conditions for a target end product based on the analysis of compositions received from the analysis subsystem. The above-described apparatus can further include a dispensing subsystem that delivers reagents, as previously described.

Specific embodiments are directed to a method of using the above-described apparatuses. The method includes providing a plurality of experimental design parameters, via control circuitry, to a dispensing subsystem and an automation subsystem for controlling a plurality of reactions within a plurality of reaction vessels. The method further includes delivering different amounts of reagents to respective reaction vessels of the plurality of reaction vessels by the dispensing subsystem and according to the experimental design parameters. The subsystem can selectively move the plurality of reaction vessels from a location proximal to the dispensing subsystem to at least one reactor module and the plurality of reactions are driven within the plurality of reaction vessels in accordance with varied reaction conditions, including exposure to different temperatures and different periods of time, as defined by the experimental design parameters and by the at least one reactor module. The method further includes analyzing the compositions contained within the plurality of reaction vessels at a speed on an order of one reaction per second and identifying optimum reaction conditions for a target end product based on the analysis.

As may be appreciated and as used herein, a target end product includes or refers to a compound, such as an organic compound, composed of two or more separate elements, and for which, the different synthetic routes are designed to reach through one or more chemical steps. Reaction screening and optimization includes or refers to screening of varied reaction conditions to identify reaction pathways that provide an optimized target end product. A dispensing subsystem, as described above, includes or refers to a system that delivers reagents to reaction vessels. Control circuitry includes or refers at least one processing circuit coupled to at least one memory circuit, such as a laptop computer, desktop computer, tablet and other computing devices. In various embodiments, the control circuitry communicates with other components of the apparatus in a wired or wireless manner. In this regard, the control circuitry can be located at the same or different location as the reactions are occurring. A reactor module includes or refers to a system that is configured to expose reaction mixtures to one or more sources of energy (e.g., energy values), such as temperatures, and thereby, drive reactions. The automation subsystem includes or refers to a mechanical system (and electrical) that moves reaction mixtures throughout the synthetic routes. The analysis subsystem includes or refers to a system that analyzes compositions after the reactions have begun.

In various embodiments, the apparatus as described above can have a throughput on the order of one reaction per second, such as up to one reaction per second. As an example, for synthetic routes that have five steps each to produce a target end product, such examples apparatuses can be used to explore potential routes and identify an optimum route having particular reaction conditions in less than two hours, such as one hour and forty minutes. Prior methods, in contrast, may take greater a month to several mounts to optimize a single synthetic route, and months to years to optimize among several synthetic routes. As used herein, a speed on an order of one reaction per second can include or refer to a range of achievable speeds (e.g., maximum speed or speeds that the apparatus is otherwise capable of achieving), such as 1.5 reactions per second to 1 reaction per 1.5 seconds and/or up to one reaction per second. In various embodiments, different speeds can be achieved, such as 1 reaction per two seconds or 1 reaction per five seconds, among other speeds. As may be appreciated, the language "up to" or "on an order of" is not intended to be limiting and various embodiments include apparatuses that are capable of achieving such speeds, and which may also be capable of achieving other speeds that are greater or less than one reaction per second.

In addition to throughputs at particular speeds, apparatuses in accordance with the present disclosure can be used to provide feedback control. The feedback control can be provided to processing circuitry of the control circuitry in less than a threshold time (e.g., instantaneous or near-instantaneous) after the analysis and used for progressive reaction design and optimization. More specifically, the feedback can be based on real-time reaction monitoring and used by the control circuitry to determine a next set of experiments for optimizing the reaction conditions and functional activity of the end products without operator intervention other than loading reagents. Such a system can perform the reactions, analysis, feedback, and repeat experiments without human intervention other than loading reagents, in various specific embodiments. In addition to reaction screening and optimization, an apparatus can be used to synthesize chemical agents and test the chemical agents in a functional assay. In such embodiments, the chemical structure and activity can all be optimized in one process.

Turning now to the figures, FIG. 1 illustrates an example of apparatus that performs reaction screening and optimization, in accordance with various embodiments. The apparatus 100 includes a plurality of reaction vessels 112, control circuitry 102, a dispensing subsystem 104, automation subsystem 106, at least one reactor module 108, and an analysis subsystem 110. The apparatus 100 can be used for synthetic design of target end products. More specifically, a plurality of synthetic routes having varied reaction conditions can be explored and used for screening or optimization of reaction conditions for reaching the target end product.

Different experimental design parameters 101 can be input to control circuitry 102 of the apparatus 100 and used to explore a plurality of synthetic routes having the varied reaction conditions for reaching a target end product. The experimental design parameters, which can also be referred to as DOE information, can include a plurality of sets of reactions conditions having different combinations of values. Example varied reaction conditions can include reagents, concentration of reagents or stoichiometry, when reagents are added, time, and temperature, among other conditions, and the values can include different actions or values of the conditions for the experiment (e.g., 50 degrees and 100 degrees). Some DOE information in accordance with the present disclosure can eliminate the use of one-reaction condition-at-a-time optimization. For example, DOE information for four experimental design parameters ($n''$) can be reduced from 256 possibilities to thirty-two experiments or reaction mixtures. As may be appreciated, the DOE information can be designed and stored as data in a memory circuit of the control circuitry 102.

The control circuitry 102 receives the experimental design parameters 101 and provides at least portions of the experimental design parameters (e.g., sets of reaction conditions) to other components of the apparatus 100, such as to the dispensing subsystem 104 and the automation subsystem 106 and for controlling reactions based on the varied reaction conditions. For example, the experimental design parameters 101 can define the varied reaction conditions, and can include a list of compounds and solvents, stoichiometry range, time and temperature conditions, and a normalized volume. The DOE information can include or be provided as a table that includes experiments to be run. In specific embodiments, a file can be generated by the control circuitry 102 and sent to the dispensing subsystem 104 for dispersing the reagents. For example, the control circuitry 102 can provide combinations of reagents and at particular concentrations to the dispensing subsystem 104 and can provide identification of a time for exposing the reaction mixtures (or a particular time for exposing each reaction mixture to a particular temperature or other type of energy used to drive the reaction) to the automation subsystem 106. The automation subsystem 106 can be provided with information about the at least one reactor module 108, such as temperature(s) the one reactor module 108 (or zones thereof) is configured to expose reaction mixtures to and/or which reactor module or zone to provide each reaction vessel to and/or for how long.

The plurality of reaction vessels 112 are configured to contain reagents taking part in a reaction that is designed to generate a target end product. A variety of types of reaction vessels 112 can be used, such as individual vials or wells. In some embodiments, the reaction vessels 112 can be placed in or form part of a substrate 114, such as a plate having the wells formed thereon and/or a plate having spaces (e.g., holes) of a size that the vials can be placed within. The substrate 114 can take a variety of forms. For example, the substrate 114 can include a tape that is flat and incorporates wells, an absorptive material to collect and mix the reagents, e.g., a Teflon or stainless steel mesh, or the plurality of vessels can formed as a well to contain the mixture. As another example, catalytic chemistry can be studied by using a palladium or other reactive metal mesh. In accordance with various embodiments, the reaction vessels 112 are independently selectable from one another (e.g., vials), and can be selectively moved for different synthetic routes. In other embodiments, at least a subset of the reaction vessels 112 are coupled together (e.g., wells on a plate) and are moved, together, for the synthetic routes.

The dispensing subsystem 104. based on the varied conditions defined by the experimental design parameters 101, delivers reagents to the plurality of reaction vessels 112 for a plurality of reaction mixtures having the varied reaction conditions. More specifically, the plurality of reaction mixtures can include different amounts or concentrations of a set of reagents, and/or different reagents. Example dispensing subsystem 104 include an inkjet printer or a liquid dispenser. As further illustrated and described herein, the inkjet printer delivers reagents based on inkjet printing. An example inkjet printer can dispense volumes of pico liter to microliter volumes to a microtiter plate using a multiple-channel print head, such as 9-channels, 12-channels, 96-channels. Each print head can contain a particular reagent. Inkjet printers can, for example, print reaction mixtures at a rate of one reaction per second. In addition, the reagents can be directly loaded into the apparatus 100. For example, pre-weighted reagents loaded in matrix tubes can be input into the apparatus 100. The pre-weighted reagents may be formatted in 96 tube tray holders that are barcoded for reagent location tracking and, optionally, sealed with inter slit-septum caps that can be directly mounted onto the print heads of the inkjet printer. Example dispensers include an inkjet printer and a print head.

However, embodiments are not limited to inkjet printers and can include a variety of different dispensing subsystems. For example, the dispensing subsystem can include a liquid dispenser that can be used to fill a plate and/or vials which are presented to the automation subsystem 106 and/or manual dispenser (e.g., pipette).

The apparatus 100 includes at least one reactor module 108 having an energy emitter, such as a thermal energy tool or radiator, that provides an energy output (e.g., heat) toward the reaction mixtures for driving the plurality of reactions. Example energy emitters include a heater, an oven, a source of microwaves or light, etc. Each reactor module has at least one zone configured to provide a particular temperature or otherwise drive the reactions differently (e.g., provide different light or microwaves). For example, the at least one reactor module 108 drives a plurality of reactions within the plurality of reaction vessels 112 according to the varied reaction conditions. In a number of embodiments, the apparatus 100 includes one reactor module that has one zone or is otherwise configured to provide a single temperature. Alternatively and/or in addition, the one reactor module can have a plurality of zones and/or the apparatus can include a plurality of reactor modules. each having one or more zones, and used to provide a plurality of different temperatures (e.g., two or more, six, ninety-six, etc.). In such example embodiments, the at least one reactor module 108 can drive a plurality of reactions within the reaction vessels 112 by exposing the reaction mixtures to different temperatures and, optionally, for different periods of time. The different periods of time can be provided via the automation subsystem 106 that moves one or more reaction vessels 112 from the at least one reactor module 108 at the end of the different periods of time. The different zones or different reactor modules can be used to drive the plurality of reactions in parallel and at a plurality of different temperatures (or other types of energy). As further illustrated and described herein, the reactor module can contain at a least a subset of reaction vessels 112 which are provided to the reactor module by the automation subsystem 106.

The automation subsystem 106 can selectively move the reaction vessels 112 and/or reaction mixtures within the reaction vessels 112 based on the experimental design parameters 101. More specifically, the automation subsystem 106 moves the reaction vessels 112 from a location proximal to the dispensing subsystem 104 to the at least one reactor module 108 for driving the reactions. As further illustrated herein, the automation subsystem 106 can include a movable arm (e.g., a robot arm) and other movable components used to selectively move the reaction vessels 112 and/or reaction mixtures. In some specific embodiments, the movement can include select movement of different reaction mixtures (e.g., vessels) to different reactor modules or zones and/or for different periods of time. In such a manner, the reaction mixtures as dispersed by the dispensing subsystem 104 are moved to the at least one reactor module 108 for driving the reactions therein, and, optionally, for different periods of time. The automation subsystem 106 can further move the reaction mixtures to a location proximal to the analysis subsystem 110 for analyzing compositions contained therein, although embodiments are not so limited, and the movement can occur using other mechanisms as further described herein. The compositions can include reactants, side products, end products, and byproducts, as well as various combinations thereof.

As a specific example, which is further described below, for reaction vessels that are individually selectable and an apparatus having multiple reactor modules or zones for providing a plurality of temperatures, the varied reaction conditions can include exposure to different temperatures for different periods of time. The automation subsystem 106 selectively moves a first subset of the plurality reaction vessels to a first location associated with the at least one reactor module 108 for exposing the first subset of vessels to a first temperature and moves a second subset of the reaction vessels to a second location of the at least one reactor module 108 for exposing the second subset of vessels to a second temperature that is different than the first. Each of the reaction vessels in the first and second subsets are moved to a location proximal to the analysis subsystem 110 upon completion of the respective reactions or as otherwise defined by the experimental design parameters 101. The movement can be by the automation subsystem 106 and/or an additional component, such as a conveyor belt as further described herein.

In accordance with a number of embodiments, the automation subsystem 106 (based on control by the control circuitry 102) can seal and/or unseal the reaction mixtures within the reaction vessels 112. For example, each of the plurality of reaction vessels 112 can be sealed prior to the plurality of reactions being driven within the reaction vessels 112 by the automation subsystem 106 and unsealed mid-reaction to introduce other reagents to sample the reaction mixture, or prior to the analysis of the compositions and based on the experimental design parameters 101. For example, the automation subsystem 106 can include the movable arm and a distribution chamber. The distribution chamber can contain a plurality of caps for the reaction vessels 112. The movable arm, along with the distribution chamber, can distribute a cap to each of the plurality of reaction vessels 112 and seal the reaction vessels using the caps. The movable arm can include or have access to a tool for subsequently unsealing the caps, as further illustrated herein.

The analysis subsystem 110 analyzes compositions contained in the plurality of reaction vessels 112 after the reactions have begun (and at any time during a set of reaction times defined by the experimental design parameters 101). The compositions can be analyzed, for example, for a particular objective or set of objectives, such as product yield, selectivity, cost, purity, m/z values and various combinations. As an example, the end products are analyzed for yield, purity, and cost, and revised reaction conditions are generated to further optimize the one or more objectives. The analysis can be at a speed on an order of one reaction per second (e.g., up to one reaction per second or more and/or the range as previously described). Example analysis subsystem include a liquid chromatography-mass spectrometer (LC-MS), such as via a 96 well plate of via UV-plate readers (in which the plates do not include vials or include transparent vials), spectroscopic images (e.g., UV-Vis vials, FT-IR cells. etc.), and direct analysis in real time (DART)-mass spectrometer (MS) via individualized vials, and various combinations thereof.

In various specific embodiments, the analysis subsystem 110 includes a DART-source (e.g., a DART-MS) that provides a beam of gas directed toward each reaction mixture surface sequentially and carries a sample of each reaction mixture into the MS of the DART-MS. The analysis beam is an ionization source (e.g., beam of gas for DART-MS), in specific embodiments, and is emitted toward each of the plurality of reaction vessels in a manner that is approximately parallel (e.g., at an angle relative to normal) to a top portion of the reaction vessels 112, although embodiments are not so limited. The beam of gas can be directed at an angle toward a top portion of the plurality of reaction vessels 112 and the gas beam carries a sampling of the reaction mixture to another component of the analysis subsystem 110 (e.g., the MS) that analyzes the compositions contained in the reaction vessels based on ions generated therefrom. The angle can include zero degrees with normal extending to the ceiling. In this manner, the reaction vessels 112, such as with a liquid from 5-10 ul and up to 20 ul (or the maximum volume of the vials), are opened and the DART head is directed across the vials directly into the MS. The beam can be directed at an angle of between 0-45 degrees to normal of the reaction vessels 112.

In some embodiments, the angle of the beam of gas can generate a detectable audio frequency signal. In such example embodiments, the apparatus 100 can optionally include sensor circuitry that outputs a signal in response to the detectable audio frequency signal to the control circuitry 102. The sensor circuitry can provide a signal in response, which is used to verify that the analysis beam is sampling (or not) each reaction mixture. For example, the control circuitry 102 can compare the detected audio frequency signal to a threshold audio signal (which indicates sampling) and therefrom verify whether analysis is occurring. In other embodiments, the apparatus 100 can include imaging circuitry used to capture a visual image of the reaction vessels 112 and from the visual image, verifies whether analysis is occurring.

In specific embodiments, the end products or other compositions can be compared to a target end product or target composition for an objective, such as selectivity and yield definitions for the target end product. The analysis subsystem 110 provides the analysis of the compositions to the control circuitry 102. The control circuitry 102 identifies optimum reaction conditions (from among the varied reaction conditions) for a target end product based on the analysis of the compositions. More specifically, the optimum reaction conditions include a set of reaction conditions among the varied reaction condition for reaching a target end product, which may include reagents, concentration of reagents, temperature, time, stoichiometry, and a combination thereof.

As previously described, the control circuitry 102 can further provide feedback control of the plurality of reactions within a threshold time. The feedback control can include or be provided by adjusting the varied reaction conditions for a plurality of additional reactions based upon comparing previous reaction results with optimal reaction product yields stored in the analysis subsystem 110 and providing the adjusted varied reaction conditions as revised experimental design parameters (e.g., a new plurality of sets of reaction conditions) to the dispensing subsystem 104 and the automation subsystem 106. The threshold period of time can include, in some specific embodiment, instantaneous or near-instantaneous control. The adjusted varied conditions can be for a plurality of additional reactions designed to reach revised optimum reaction conditions for the target end product and/or other target compositions (e.g., optimize one or more objectives). The control circuitry 102 can provide the feedback control, e.g., the adjusted varied reaction conditions, as revised experimental design parameters to the dispensing subsystem 104 and the automation subsystem 106. The apparatus 100 uses the revised experimental design parameters to run an additional test and further optimize reaction conditions from an analysis of the compositions therefrom.

The feedback control can provide the adjusted varied conditions using machine learning. For example, the control circuitry 102 is trained with data for molecular properties, such as the ability to inhibit an enzyme, act as an antimicrobial, catalyze a particular reaction, and predicting if a molecule has a relevant property. Over time, the control circuitry 102 updates its training to predict what reaction conditions and/or values thereof impact particular objectives. The control circuitry 102 is updated over time and uses this training to provide adjusted varied reaction conditions for one or more objectives and to further optimize the reaction conditions, as described above.

As a specific example, and which is consistent with the above-provided specific example, the plurality of reaction vessels 112 include individual and separable reaction vessels. The automation subsystem 106 places the reaction vessels 112 into a substrate 114 that is proximal to the dispensing subsystem 104. The dispensing subsystem 104 dispenses different amounts of reagents to respective reaction vessels of the plurality according to the experimental design parameters 101. The plurality of reaction vessels 112 with the reaction mixtures are sealed via the automation subsystem 106, such as via the above-described and further illustrated caps. The reaction vessels 112 are selectively moved by the automation subsystem 106 from the substrate 114 that is proximal to the dispensing subsystem 104 to the at least one reactor modules 108. The automation subsystem 106 moves specific vessels to different zones or reactor modules that are associated with different temperatures. For example, a first subset of the plurality of reaction vessels are moved to a first zone and/or first reactor module which drives the reactions within the first subset of reaction vessels by exposing the reaction mixtures to a first temperature (e.g., 50 degrees C.). A second subset of reaction vessels are moved to a second zone and/or a second reactor module, which exposes the second subset of reaction vessels to a second temperature (e.g., 75 degrees C.). A third subset are moved to a third zone and/or third reactor module and exposed to a third temperature. Embodiments are not limited to three zones, reactor modules and/or temperatures, and can include more or less than three, such as one, two, four, five, six, twenty, etc., zones, reactor modules, and/or temperatures.

Additionally, in various embodiments, respective reaction mixtures of the subset can be exposed to the respective temperatures for different periods of time. For example, the automation subsystem 106 can selectively move (e.g., remove from the exposure to the temperature) reaction vessels from the at least one reactor module 108 at different times based on the experimental design parameters 101. Using the above-provided example, a first reaction vessel in the first subset is removed from the first zone and/or first reactor module after expiration of a first period of time (e.g., 2 minutes) and a second reaction vessel in the first subset is removed from the first zone and/or first reactor module after expiration of a second period of time (e.g., 2 minutes and twenty seconds). Although embodiments are not so limited, and the plurality of reaction vessels can be moved at the same time or at different periods of time to a location proximal to an analysis subsystem 110 responsive to the plurality of reactions being driven to completion. For example, the automation subsystem 106 can unseal the plurality of reaction vessels 112 and selectively move reaction mixtures proximal to the analysis subsystem 110. The analysis subsystem 110 can then analyze the compositions, as compared to the target end product. In various embodiments, the reaction vessels 112 can be unsealed by uncapping the reaction vessels 112 (e.g., removing the cap that seal the reaction vessels 112) or piercing a seal of the reaction vessels 112. For example, the reaction vessels 112 can include a seal that has a puncturable location that can be punctured to facilitate product retrieval and analysis.

The movement can be by the automation subsystem 106. For example, for interfacing with a DART-MS, the reaction vessels 112 can be placed on the substrate 114. such as a 96-well plate. The automation subsystem 106 caps the reaction vessels 112, places the capped reaction vessels into the at least one reactor module 108 as defined by the DOE information, and then removes them from the at least one reactor module 108. The automation subsystem 106 uncaps (or puts in a position to uncap) the reaction vessels 112, and sequentially locates the uncapped reaction vessels in front of the DART inlet. For example, automation subsystem 106 can place the uncapped reaction vessels on a conveyor that sequentially transports the reaction vessels in front of the DART inlet, as further illustrated herein.

In accordance with a number of embodiments, one or more of the synthetic reaction routes can include adding reagents at different times. In such embodiments, one or more reaction vessels are moved from the at least one reactor module 108, unsealed or uncapped, moved back to the dispensing subsystem 104 for dispensing one or more additional reagents, and optionally, recapped and moved back to one of the at least one reactor module 108 for further driving the reaction. The automation subsystem 106 selectively moves the reaction vessels from the at least one reactor module 108 and/or the dispensing subsystem 104 to a location in front of the DART-MS. In another embodiments, the reaction vessels are returned to the substrate 114 or an additional substrate, e.g., well plate, and then the substrate is moved with an X-Y stage to position the vials in front of the DART-MS.

Although the above example describes use of a DART-MS, embodiments are not limited to DART-MS, to varied reaction conditions that include different temperatures and times, and/or to reaction vessels that can be individually moved. For example, the reaction mixtures can be dispensed in individual reaction vessels, capped, and reacted, as described above. The automation subsystem 106 can replace the reaction vessels, as uncapped or otherwise unsealed (e.g., punctured), on or to the substrate 114, and the reaction mixtures can be sampled directly with the LC-MS. In other embodiments, the reaction vessels are not vials that are individually selectable and/or movable. For example, the reagents can be dispensed directly into a substrate 114 having wells, such as a microtiter well plate. The substrate 114 (e.g., plate) can be a traditional solid plate or a plate is compatible with a UV plate reader. In some embodiments, the apparatus 100 is run in a screening mode in which all wells are exposed to the same temperature and the same time. In a screening mode, a variation of input reagents can be tested to identify which chemistries work. The dispensing subsystem 104 dispenses the reagents into the well plate. For example, the plate is transported to the at least one reactor module 108 for treatment (if needed), and then is placed on an LC-MS autosampler. In other embodiments, the reagents are dispensed into a transparent microtiter plate. The reaction mixtures are reacted with one set of reaction conditions and put on a plate reader for rapid UV/Vis assessment. In other specific embodiments, the (individual) reaction vessels 112 include transparent vials where the reagents are dispensed, reacted individually (optimization), and then replaced on a transparent plate for UV/Vis analysis, such as described above.

Figure 2A:
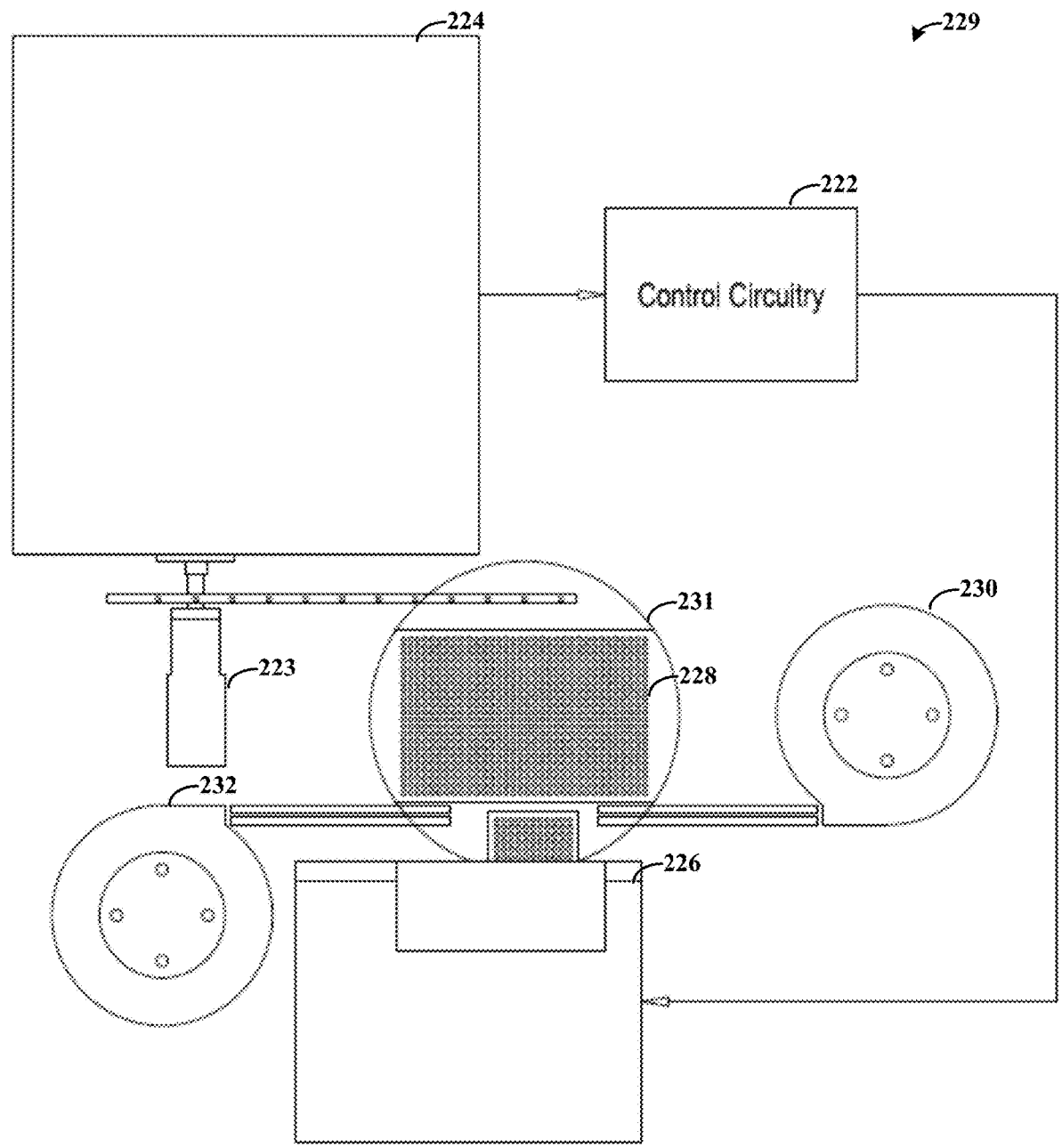
FIGS. 2A-2E illustrate example apparatuses that performs reaction screening and/or optimization, in accordance with various embodiments.

FIG. 2A illustrates another example apparatus, in accordance with various embodiments. As illustrated and previously described in connection with FIG. 1, the apparatus 229 includes control circuitry 222, at least one reactor module 228, an automation subsystem, a dispensing subsystem 226, and an analysis subsystem 224. For clarity purposes, the automation subsystem (e.g., the movable arm) is not illustrated in FIG. 2A. The space accessible by the automation subsystem is defined by the area 231.

The apparatus 229 optionally includes a plurality of distribution chamber 230, 232. A first distribution chamber 230 can contain the plurality of reaction vessels and can be used to distribute the reaction vessels to the substrate that is proximal to the dispensing subsystem 226. For example, a first conveyor can be coupled to the first distribution chamber 230. The first distribution chamber 230 distributes, one at a time, the reaction vessels to the first conveyor that moves the reaction vessels proximal to the substrate. The automation subsystem places the respective vessels into the substrate for dispersal of the reagents by the dispensing subsystem 226. The second distribution chamber 232 can contain the plurality of caps for the reaction vessels. The movable arm, along with the second distribution chamber 232, can distribute a cap to each of the plurality of reaction vessels. For example, the second distribution chamber 232 is coupled to a second conveyor, and distributes, one at a time, the caps to the second conveyor that moves the caps proximal to the substrate. The automation subsystem can seal the reaction vessels using the caps while the reaction vessels are located on the substrate (or alternatively after moving to the reactor modules), and selectively moves the reaction vessels to the at least one reactor module 228, such as moving to different zones or different reactor modules used to expose the reaction vessels to different temperatures.

The automation subsystem can additionally move the reaction vessels proximal to the analysis subsystem 224. In specific embodiments, the analysis subsystem 224 is coupled to a third conveyor. The automation subsystem selectively uncaps or otherwise unseals and moves reaction vessels (optionally, at different times according to the DOE information) to the third conveyor. The reaction vessels are sequentially brought in proximity to an analysis beam of the analysis subsystem 224, such as an ion beam provided by a DART-MS head 223, as previously described.

Figure 2B:
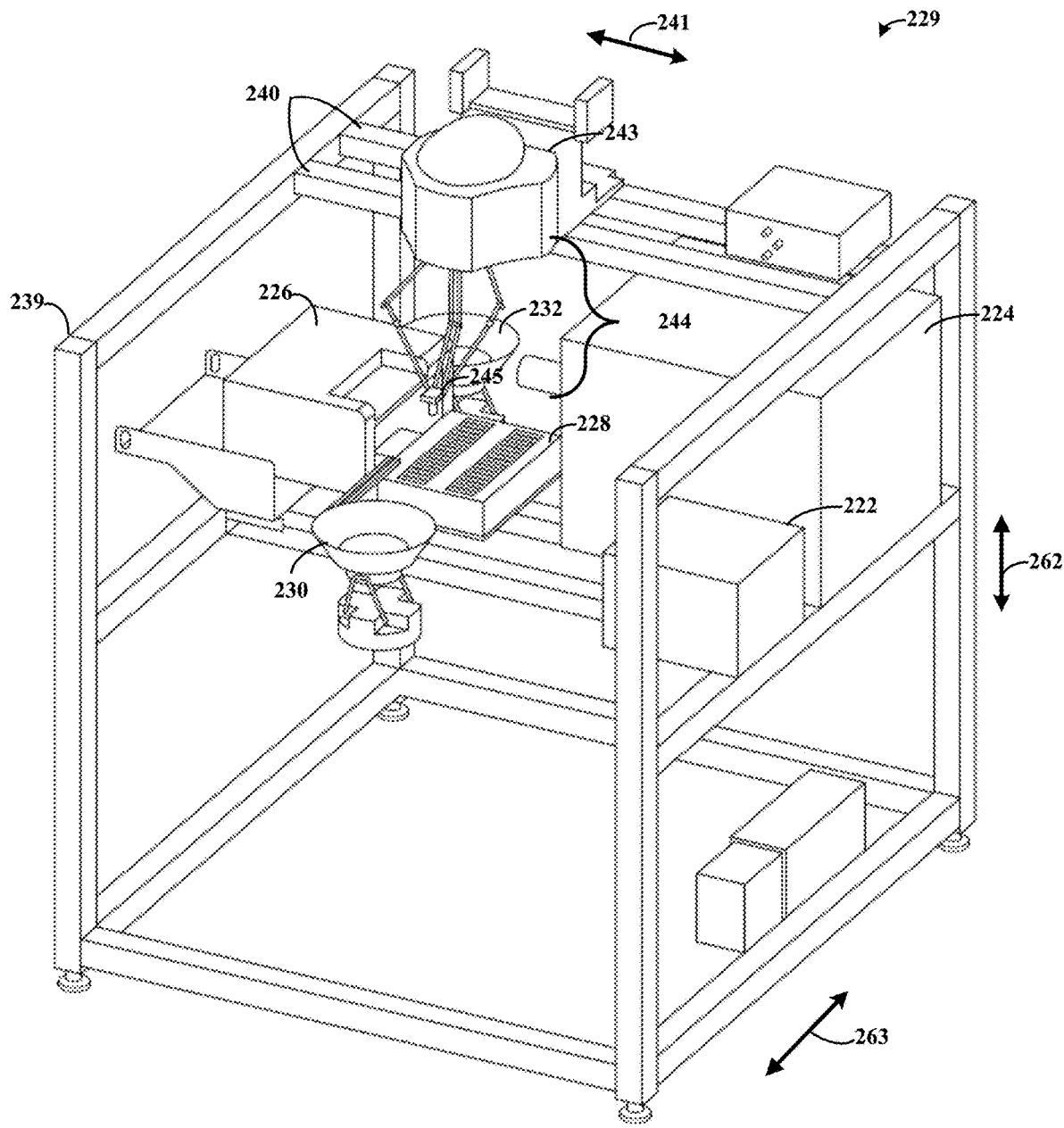

FIG. 2B illustrates an example apparatus having an automation subsystem, in accordance with various embodiments. As illustrated, the automation subsystem of the apparatus 229 can include a movable arm 244 coupled to an actuator 243, such as a motor. The movable arm 244 has a head assembly 245 at one end and is coupled to the actuator 243 at the other. The head assembly 245 is used to selectively pick up reaction vessels and/or a substrate, and move the reaction vessels or substrate, such moving to the at least one reactor module 228, a conveyor, and/or proximal to the analysis subsystem 224. The movable arm 244 can include one or more interconnected sets of links and power joints that can be moved via power from the actuator 243. The actuator 243 controls movement of the movable arm 244 and/or the head assembly 245 via a power source by converting electrical energy to effect the movement. The control circuitry 222 of the apparatus 229 can provide signals to the actuator 243 and/or the automation subsystem can include additional processing resources used to provide the signals for movement responsive to instructions provided from the control circuitry 222.

In various embodiments, the movable arm 244 and actuator 243 allows for movement of the movable arm 244 in an x or a y direction (e.g., first direction 241), and the movable arm 244 can further move the head assembly 245 in an x, y, and z direction (e.g., the directions 241, 262, and 263). In such embodiments, the movable arm includes a robotic arm. For example, the various components of the apparatus 229 can be mounted to framework 239, such as the dispensing subsystem 226, the analysis subsystem 224, the at least one reactor module 228, and optionally, the one or more distribution chambers 230, 232. More specifically, a set of tracks 240 are mounted to the framework 239 and the actuator is coupled to the set of tracks 240. although embodiments are not so limited.

In other specific embodiments, in the alternative to a robotic arm, the movable arm 244 is coupled to a gantry that allows for the movement of the movable arm 244 in the x and/or y direction (such as illustrated by FIG. 10). The gantry includes or is otherwise coupled to the set of tracks 240 that are mounted to the framework 239 and elongate in a first direction 241, e.g., in an x or y direction. The framework 239 can be perpendicular to the set of tracks 240, although embodiments are not so limited and the framework can be at a variety of angles to the set of tracks. The set of tracks 240 can be parallel to one another and the actuator 243 is mounted to the set of track 240, with the movable arm 244 coupled thereto. The actuator 243 (and thus the movable arm 244) can travel along the set of tracks 240 in the first direction 241. The movable arm 244 allows for movement of the head assembly 245 in two or more directions 241, 262, 263 (e.g., x, y, and/or z), allowing for the head assembly 245 to move to different locations between and outside the set of tracks 240 in two-dimensional and three-dimensional directions. As further illustrated herein, the head assembly 245 can select (e.g., pick up) a specific reaction vessel and/or a substrate and move the selected reaction vessel or substrate to another location. The movable arm 244 and head assembly 245 can thereby move reaction vessels, reaction mixtures, substrates, and/or caps to various portions of the apparatus 229.

The head assembly 245, as illustrated in further detail herein, can include an interface tool used to grab reaction vessels, substrates, and/or caps, and interact therewith. In specific embodiments, the head assembly 245 couples to one or more links and/or power joints of the movable arm 244 (e.g., a robotic arm). The interface tool can interact with the various components, such as moving the components to other locations, sealing the reaction vessels with the caps, removing the caps, etc. In specific embodiments, the interface tool has a pressure source used to apply positive and/or negative pressure to select and move a reaction vessel, substrate, and/or to seal or unseal the reaction vessels. As a specific example, the head assembly 245 can apply a negative pressure when located proximal to (e.g., above) a reaction vessel to select (e.g., suction) and move the reaction vessel to another location and removes the negative pressure and/or applies a positive pressure to release the reaction vessel when the reaction vessel is at the other location. The reaction vessel can be sealed by applying a pressure to the cap when the cap is located proximally to the top of the reaction vessel. However, embodiments are not so limited, and in some embodiments the head assembly 245 includes an interface tool having multiple links, and optionally, joints (e.g., finger-like components) that form a robot hand or gripper used to grab a reaction vessel, substrate, and/or cap, and move the same. Additionally, the movable arm 244 can include more or fewer sets of links or joints than illustrated.

In accordance with various embodiments, the gantry can be used to move the movable arm 244 and head assembly 245 to different locations using a variety of mechanisms, such as one or more rotors coupled to components of the gantry (e.g., the set of tracks 240) and the actuator 243. For example, rotation of the rotor moves the actuator 243, and the movable arm 244 coupled thereto, in the first direction 241. The movable arm 244 can provide additional movement of the head assembly 245. Other movement mechanisms, as would be appreciated by one of ordinary skill in the art, can include rotating wheels or other types of rotating components, gears and/or rotary gear systems, pulleys, crank and shafts and/or crankshafts and rods, collars, couplings, cams, clutches, flywheels, shaft ends, spindles, meshing gears, and horizontal or vertical shafting, among other types of mechanisms.

Although the gantry illustrated by FIG. 2B has a set of tracks 240 mounted to the framework 239, embodiments are not so limited. For example, a single track can be between the framework 239. and that elongates in the first direction 241. The actuator 243 or other components of the automation subsystem can be attached to and travel along the single track via one or more rotors, slides or other movement mechanisms, as provided above. Additionally, various embodiments may not include a gantry, and the movement can be provided by the movable arm 244 and the actuator 243 (e.g., forming a robotic arm).

As described above, the movement of the movable arm 244 and/or head assembly 245 can be provided in a variety of ways. In some specific embodiments, the movement may be provided without moving the actuator 243 along the set of tracks 240 (or single track) of the gantry. The movement can, for example, be provided via rotational movement of the movable arm 244 (e.g., a robot arm that rotates in a circular motion). For example, the movable arm 244 is coupled to the actuator 243 via a rotary joint that twists, swings, and/or bends to provide circular motion, like a human elbow. The movable arm 244 can provide the above-describe movement of reaction vessels, substrates, and/or caps, among other functionalities, by moving the head assembly 245 to different locations via the rotary joint. Various embodiments can include combinations of the above.

The movable arm 244, in specific embodiments, can have a default position which is used to align the movable arm 244 and head assembly 245 within the apparatus 229. The default position can include a predefined location (e.g., a home or zero position) in the apparatus 229 that the movable arm 244 and/or head assembly 245 moves to or is located in when the apparatus 229 is not running a test. In specific embodiments, the default position can include specific X, Y, and Z coordinate locations.

Figure 2C:
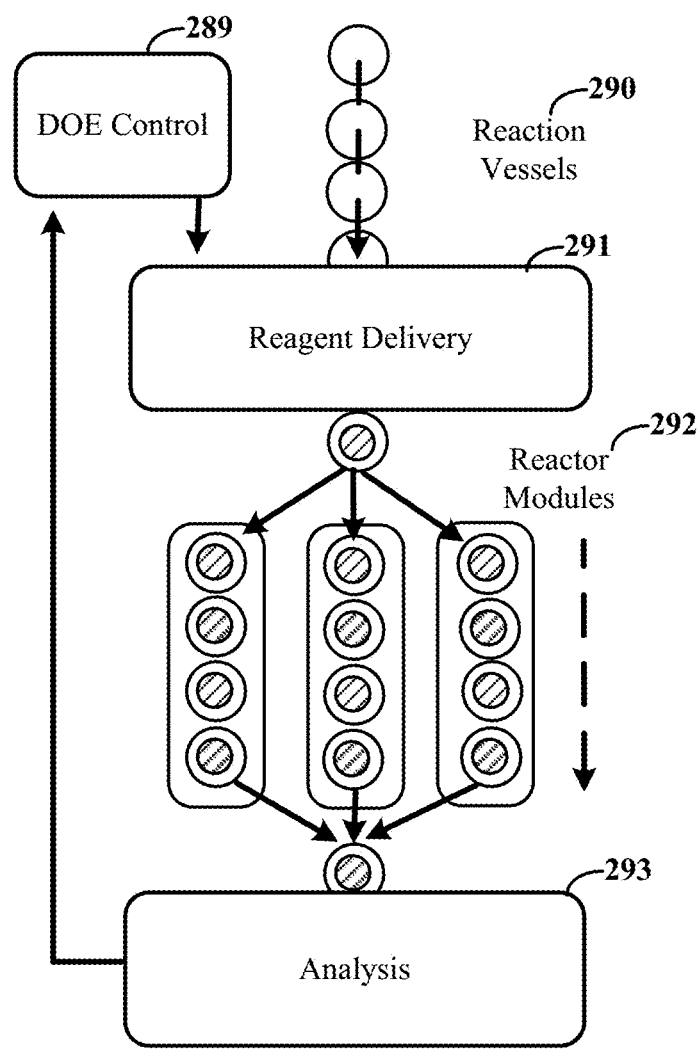

FIG. 2C illustrates an example of parallel operating reactor modules, in accordance with various embodiments. As previously described, the apparatuses illustrated herein can be used for reaction screening and optimization. Such apparatuses provide reagent delivery of reaction mixtures into reaction vessels 290 according to DOE control 289 (e.g., via control circuitry providing DOE information). The reagent handling and delivery 291 can include a multi-port pump system, such as various inkjet printers. In various embodiments, the print heads or pumps can be disposable. The reagent handling can print reaction mixtures at a speed on an order of one reaction per second or faster. As illustrated, the reaction processing allows for evaluation of each individual reaction and, in some specific embodiments, allows for parallel processing of a plurality of varied reaction conditions via a plurality of reactor modules 292. The analysis, at 293, of the compositions can be performed on a time scale similar to the reagent delivery and can mitigate sample handling. In addition, the analysis can provide for control feedback that allows for automation of reaction screening process for multi-step routes using machine learning, such as via building of a chemical database. The optimization can be for one or more objectives, such as optimal reaction product yields, costs, time for reactions, and/or other parameters.

Figure 2D:
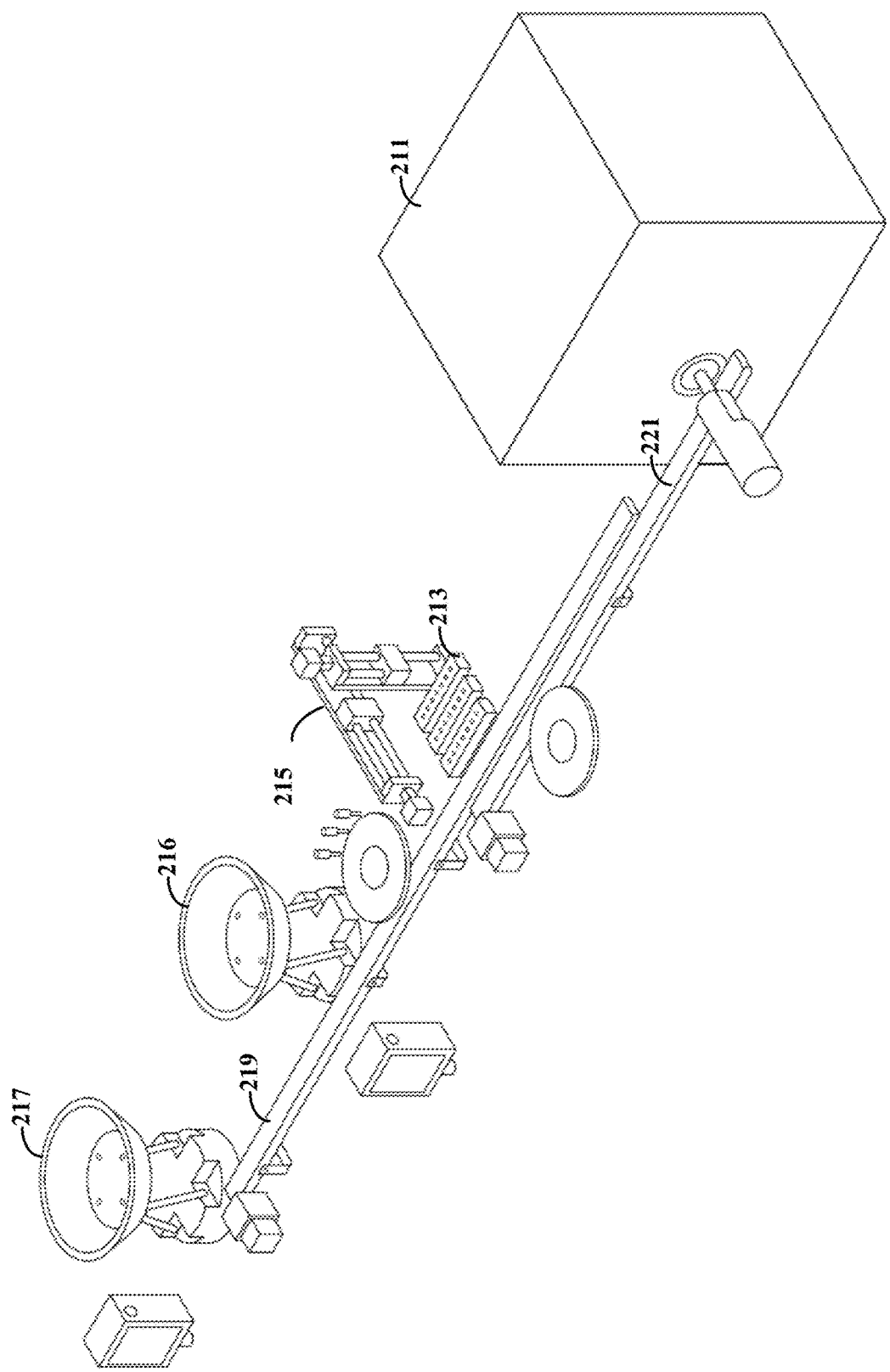

FIG. 2D illustrates an example apparatus, in accordance with various embodiments. As illustrated, the apparatus can include one or more conveyors 219, 221 used to move the reaction vessels in addition to an automation subsystem 215 (at least a portion of is illustrated by FIG. 2D). The apparatuses in accordance with the present disclosure optionally include two or more distribution chambers 217, 216 used to distribute reaction vessels and caps, as previously discussed. For example, the first distribution chamber 217 distributes reaction vessels to a first conveyor 219 that moves the reaction vessels proximal to a dispensing subsystem (not illustrated). The automation subsystem optionally moves the reaction vessels to a substrate for the dispensing subsystem to disperse reagents to form a plurality of reaction mixtures (although not illustrated by FIG. 2D). The second distribution chamber 216 distributes caps (optionally to a second conveyor) for dispersing and sealing the reaction vessels.

The automation subsystem 215 can include a gantry and movable arm. The gantry has an x-y stage coupled to the movable arm having a head assembly used to selectively move reaction vessels to the at least one reactor module 213 (and optionally different zones) for exposing the reaction mixtures to one or temperatures and for one or more different periods of time. As previously described, an actuator can be used to provide power for moving the gantry (e.g., the x-y stage) and the movable arm, and to select reaction vessels by the head assembly. The automation subsystem 215 can uncap the reaction vessels and move the reaction vessels (or moves the reaction mixtures to a substrate) to another conveyor 221 that moves the reaction mixtures toward the analysis subsystem 211 for analysis of the compositions therein.

Figure 2E:
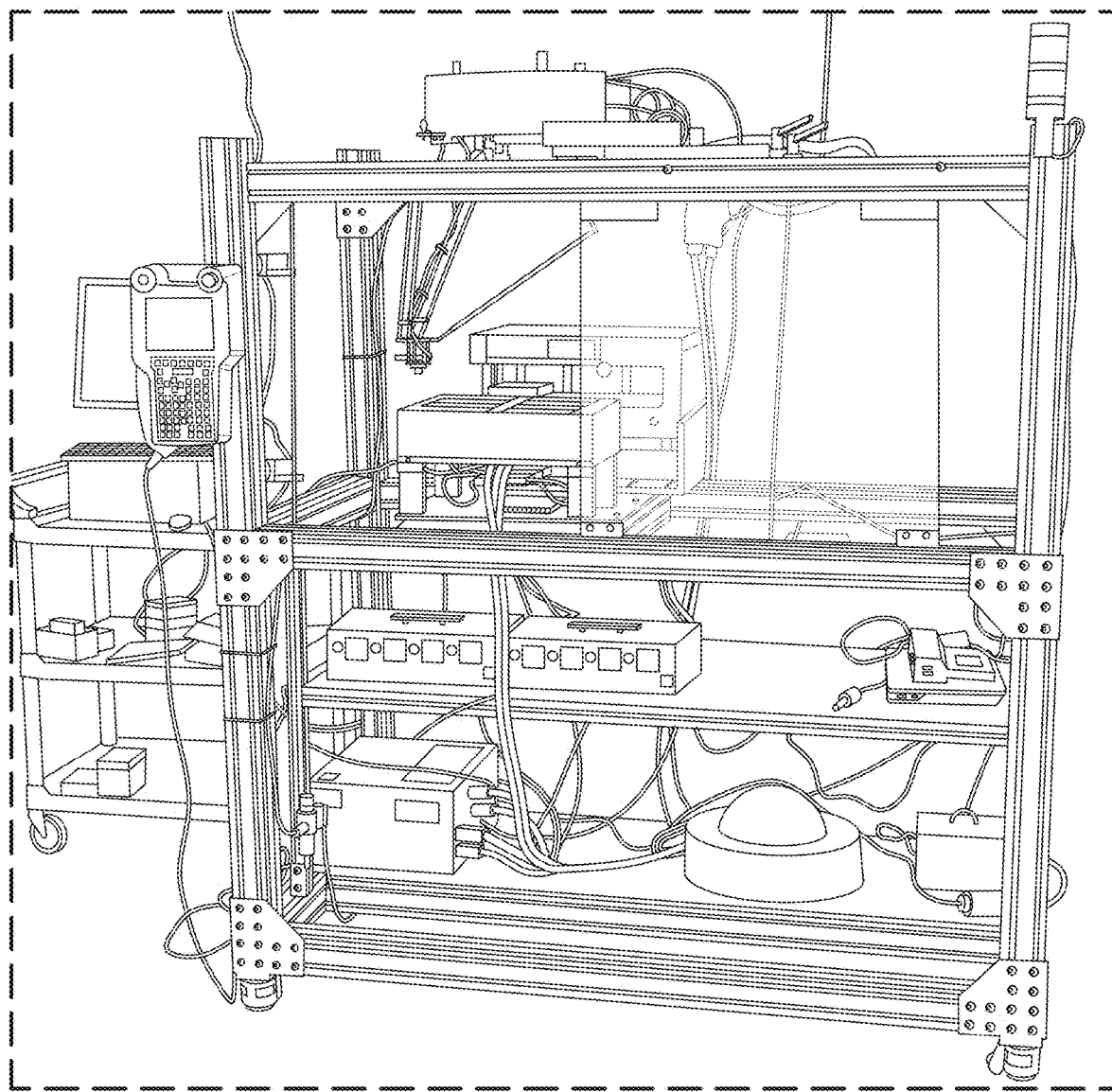

FIG. 2E illustrates the example apparatus of FIGS. 2A-2B with placement of the automation subsystem, in accordance with various embodiments. The automation subsystem, as illustrated and previously described, can include the movable arm (e.g., a robotic arm) that can selectively move the reaction vessels throughout the apparatus. More specifically, FIG. 2E is an image of an experimental embodiment of an apparatus that is consistent with the apparatuses illustrated and described by FIGS. 2A-2B.

FIGS. 3A-3D illustrate an example of an automation subsystem moving reaction vessels from a location proximal to the dispensing subsystem to the at least one reactor module, in accordance with various embodiments. The automation subsystem can be part of the apparatus as previously described in connection with FIGS. 2A-2B. As illustrated, the automation subsystem can move a first reaction vessel 348 to a first location 350 associated with the at least one reactor module and move a second reaction vessel 349 to a second location 351 associated with the at least one reactor module. The first and second location 350, 351 can be associated with the same reactor module or zone of a reactor module (e.g., are exposed to the same temperature) or with different reactor modules or zones of a reactor module (e.g., are exposed to different temperatures or other energy sources).

Figure 3A:
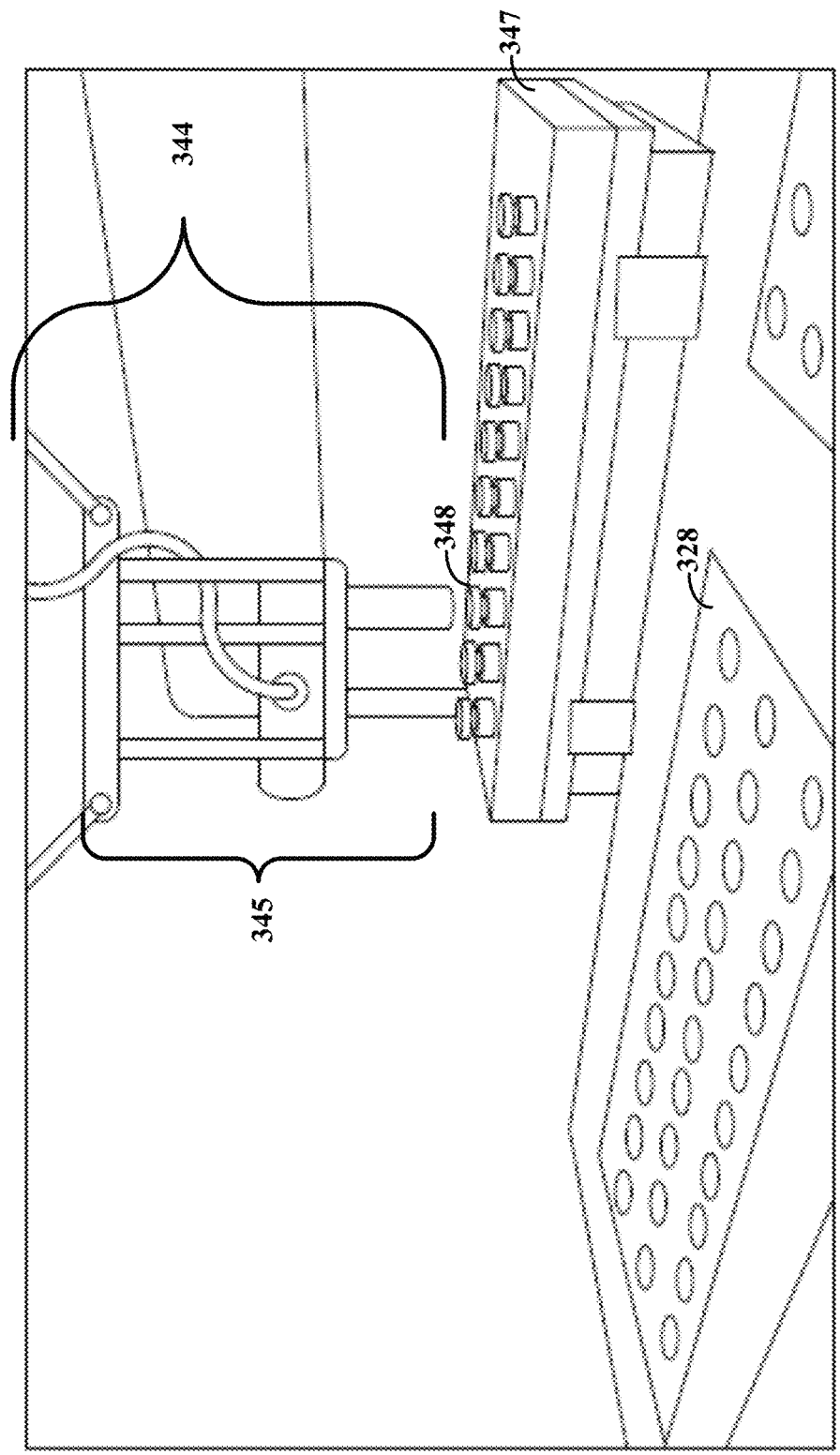
FIGS. 3A-3D illustrate an example of an automation subsystem moving reaction vessels from a location proximal to the dispensing subsystem to the at least one reactor module, in accordance with various embodiments.
Figure 3B:
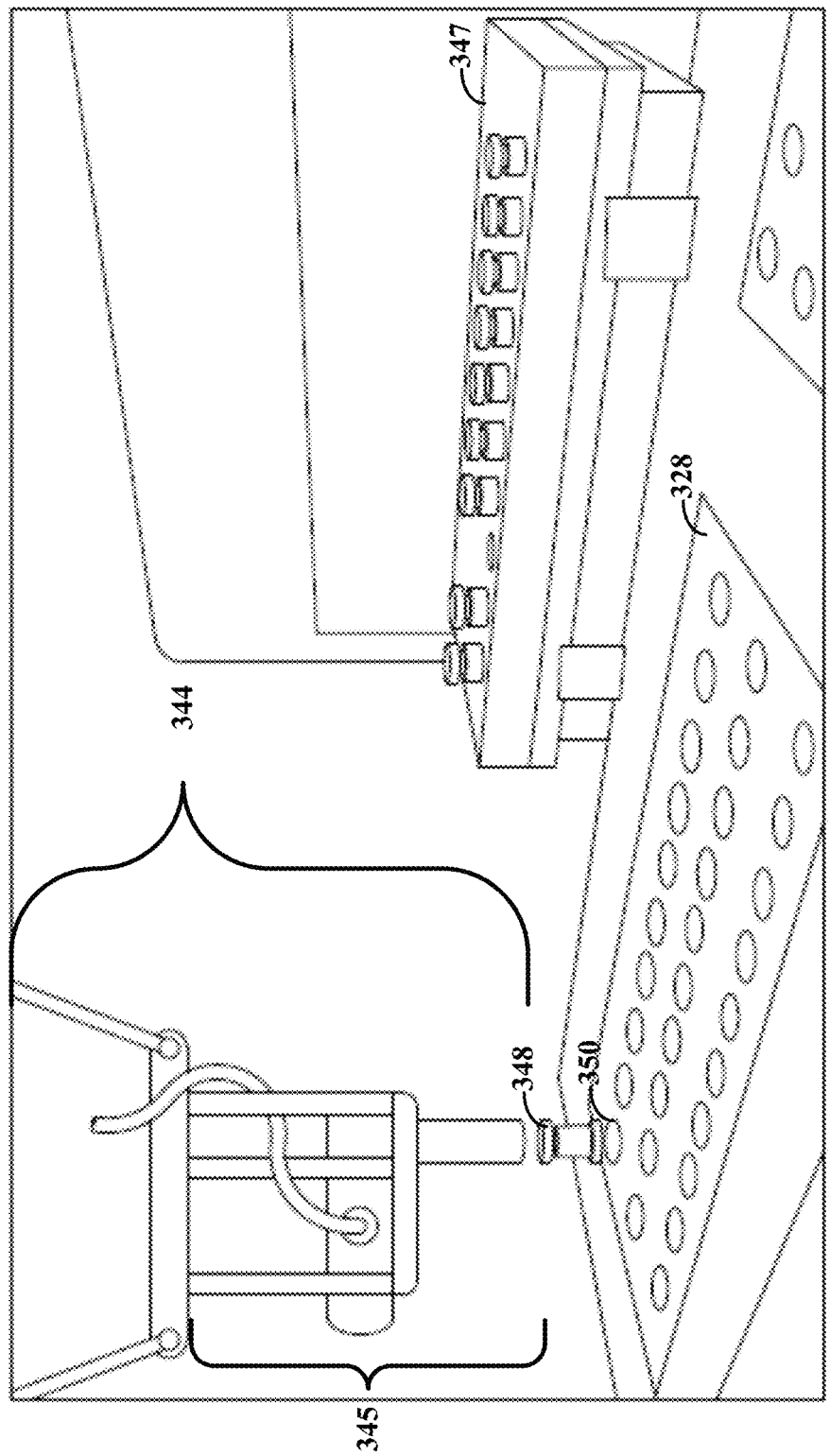
Figure 3C:
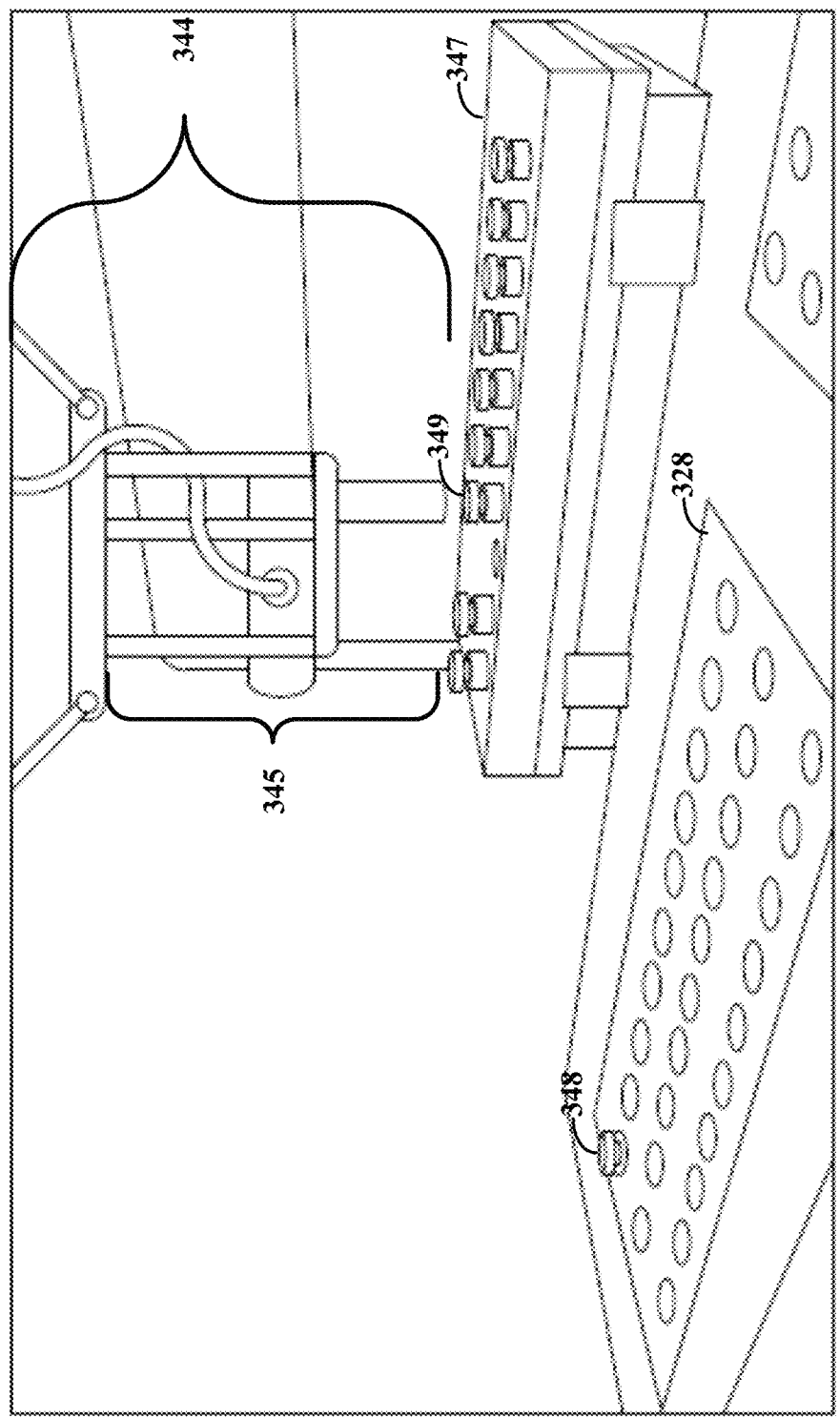
Figure 3D:
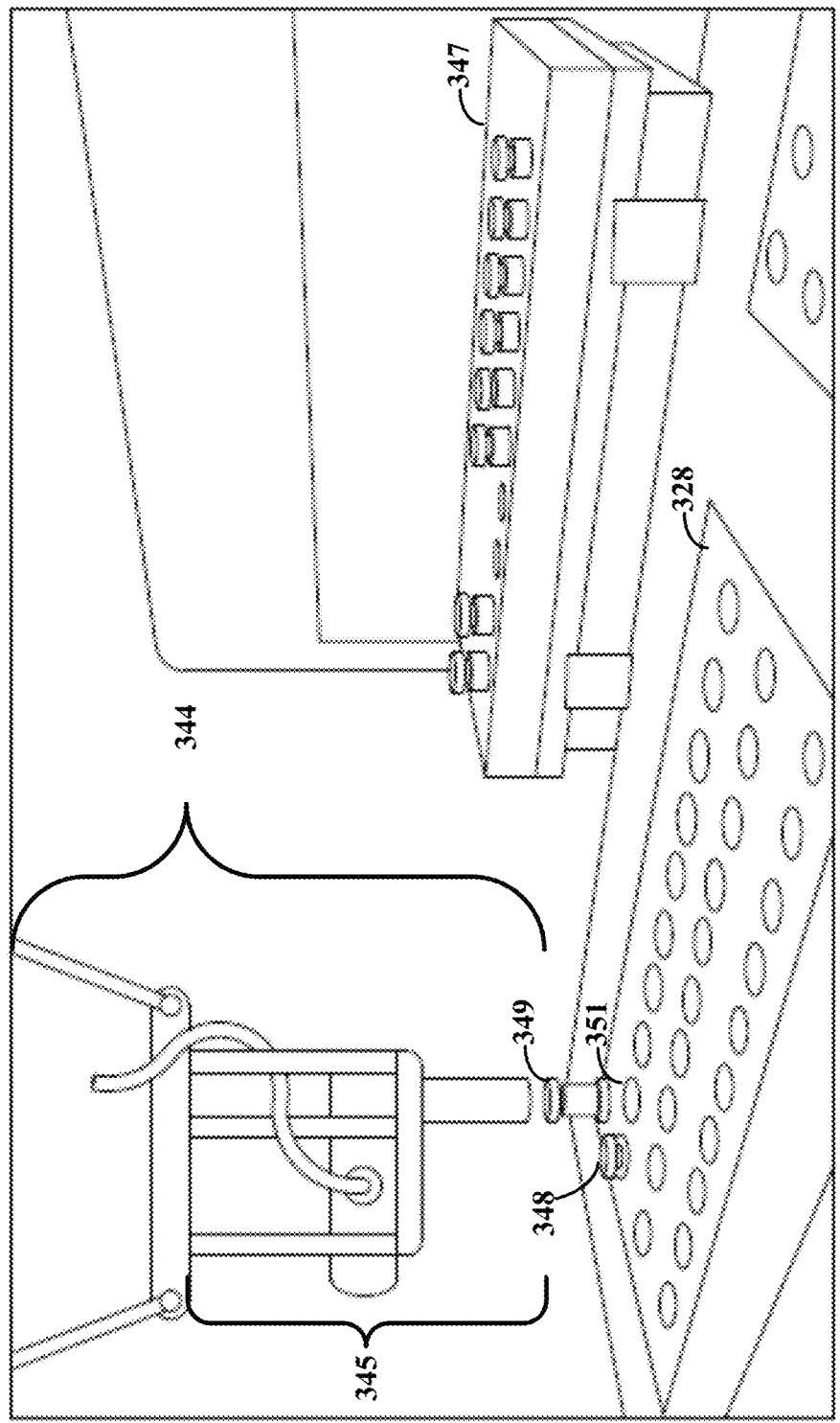

More specifically, the movable arm 344 including the head assembly 345 of the automation system are used to select the first reaction vessel 348 that is located proximal to the dispensing subsystem (e.g., in a substrate 347 proximal to the dispensing subsystem substrate), as illustrated by FIG. 3A, and move the first reaction vessel 348 to a first location 350 associated with the at least one reactor module 328, as illustrated by FIG. 3B. The movable arm 344 including the head assembly 345 can select the second reaction vessel 349 that is located proximal to the dispensing subsystem (e.g., in the substrate 347 proximal to the dispensing subsystem substrate), as illustrated by FIG. 3C, and move the second reaction vessel 349 to a second location 351 associated with the at least one reactor module 328, as illustrated by FIG. 3D.

Figure 4:
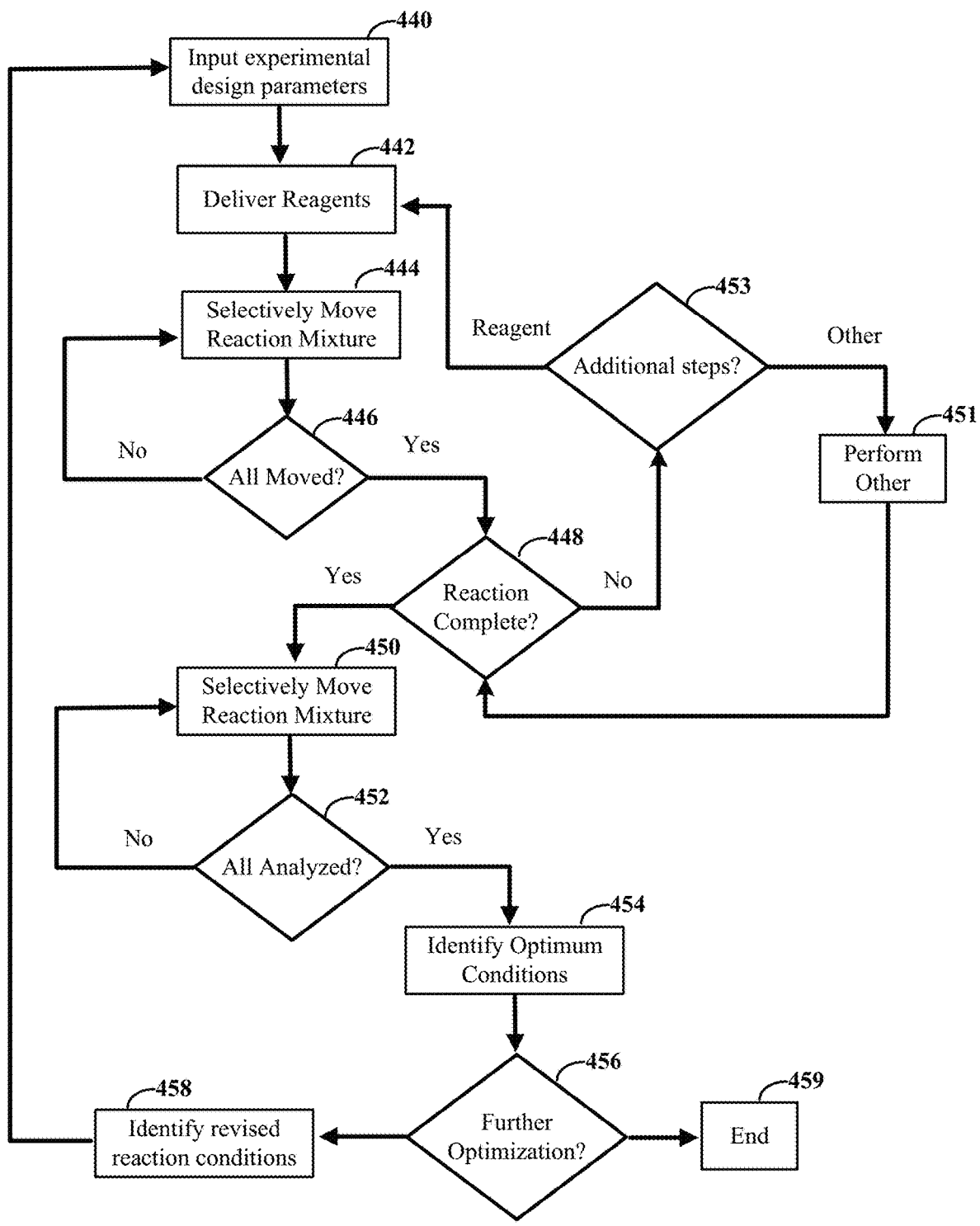
FIG. 4 illustrates an example method for reaction optimization, in accordance with various embodiments.

FIG. 4 illustrates an example method for reaction optimization, in accordance with various embodiments. Experimental design parameters are input to control circuitry and provided to a dispensing subsystem and automation subsystem for controlling a plurality of reactions within a plurality of reaction vessels, at 440. As previously described, the experimental design parameters include a plurality of sets of reaction conditions for a plurality of reactions. Each of the reactions can have a different combination of values of the reaction conditions such that the plurality of reactions have varied reaction conditions for reaching a target end product. As an example, if the varied reactions conditions include temperatures of 50 degrees and 100 degrees with different concentrations of reagent A and B of respectively 50:50, 75:25, and 25:75, the experimental design parameters include reactions with varied conditions of: 50 degrees, 50:50 of reagent A and reagent B; 50 degrees, 75:25 of reagent A and reagent B; 50 degrees, 25:75 of reagent A and reagent B; 100 degrees, 50:50 of reagent A and reagent B; 100 degrees, 75:25 of reagent A and reagent B; and 100 degrees, 25:75 of reagent A and reagent B. As illustrated, the reactions may not include repeats of combinations of reaction conditions. As may be appreciated by one of ordinary skill, the above provided example includes two conditions that are varied with two variations and results in six reactions, however embodiments are not so limited and can include a greater number of varied conditions and greater variations for each reaction condition. Additionally, to identify the optimum conditions, each combination of varied reaction conditions may not be generated. For example, the combinations (e.g., sets of reaction conditions) can be reduced to a manageable set, such as a four parameters study with 256 possibilities being reduced to thirty-two experiments (or sets of varied conditions). Compositions formed by the reactions can be analyzed to determine optimum reaction conditions from the reaction conditions in the plurality of sets.

Based on the experimental design parameters, at 442, the method includes delivering the reagents to the reaction vessels. The delivery can include different amounts (e.g., concentrations) of reagents delivered to respective reaction vessels of the plurality of reaction vessels by a dispensing subsystem and according to the experimental design parameters. In specific embodiments, an automation subsystem can provide (e.g., place) each of the reaction vessels in a substrate (e.g., 96-well plate) for delivery of the reagents and, after delivery, can seal each reaction vessel using distributed caps.

The method further includes selectively moving the plurality of reaction vessels from a location proximal to the dispensing subsystem to at least one reactor module by the automation subsystem, at 444. The selective movement can include moving the entire substrate or individual reaction vessels, in various specific embodiments. For example, the automation subsystem can selectively move a reaction mixture by moving a first reaction vessel to the at least one reactor module, such as a first zone of a reactor module or a first reactor module. The first reaction vessel can be associated with a set of reaction conditions having a first temperature that the first zone or first reactor module can expose the reaction mixture to. Different reaction vessels and/or reaction mixtures can be moved to different zones of the reactor module or different reactor modules that can expose reaction mixtures to different temperatures. Using the above provided example, a second reaction vessel is moved to a second zone of the reactor module or to a second reactor module that exposes reaction mixtures to a second temperature. At 446, a determination can be made on whether or not all reaction mixtures have been moved. If each of the reaction mixtures are not moved, the method includes selectively moving additional reaction mixtures until all mixtures are moved, at 444.

As previously described, the plurality of reactions is driven by the at least one reactor module. The at least one reactor module can expose one or more of the reaction mixtures to one or more temperatures in accordance with the varied reaction conditions. In specific embodiments, the plurality of reactions is driven in accordance with varied reaction conditions that include exposure to different temperatures and/or for different periods of time (and, optionally, adding reagents at different times), as defined by the experimental design parameters.

The apparatus can determine if a reaction is complete, at 448. In response to determining a reaction is not complete, at 453, the method includes determining (by the control circuitry) what additional steps are to be taken and performing the steps, at 451. Such additional steps can include adding additional reagents, continuing to expose the reaction mixture(s) to a temperature, exposing the reaction mixture(s) to another temperature, and/or other actions. For example, if the additional step includes adding a reagent to the reaction mixture, the method can include, optionally, uncapping or otherwise unsealing the reaction vessel (if sealed), moving the reaction vessel or reaction mixture to the substrate proximal to the dispensing subsystem, and dispersing the additional reagent(s) to the reaction vessel. The reaction vessel is selectively moved either to the at least one reaction vessel or the analysis subsystem (if the reaction is complete).

In response to a reaction being complete in accordance with the experimental design parameters, the reaction mixture and/or reaction vessel is selectively moved from the at least one reactor module to the analysis subsystem, at 450. The movement can be by the movable arm of the automation subsystem and/or a conveyor, as previously described. In some specific embodiments, the automation subsystem unseals (e.g., uncaps) the reaction vessels prior to analysis and/or movement. The analysis is performed by an analysis subsystem, such as an LC-MS and/or DART-MS, as previously described. The compositions can be analyzed for one or more objectives, such as product yield and purity.

At 452, a determination is made whether each of the reaction vessels/reactions are analyzed. If not, reaction vessels are further moved for the analysis, at 450. In response to determining all compositions are analyzed, at 454, the method further includes identifying optimum reaction conditions for the target end product based on the analysis. The optimized reaction conditions include a set of values of the reaction conditions from the varied reaction conditions that reach the target end product at an optimum value of one or more objectives (e.g., yield and/or cost) from the plurality of sets of reactions conditions.

In various embodiments, feedback control can be provided. For example, feedback control can include identifying if further optimization is to be performed, at 456, such as identifying additional varied conditions to tests based on the compositions analyzed. In specific embodiments, the results can be compared with optimum reaction product yields stored in the analysis subsystem and/or control circuitry. In response to determining no further optimization is to be run, the process ends, at 459. In response to further optimization, at 458, the control circuitry adjusts the varied reaction conditions for a plurality of additional reactions based upon comparing previous reaction results with optimal reaction product yields (or other objectives) stored in the analysis subsystem and provides the adjusted varied reaction conditions as revised experimental design parameters to the dispensing subsystem and the automation subsystem. The revised experimental design parameters are used to run the additional test and further optimize the reaction conditions for formation of the target end product. As an example, the compositions, such as end products, are analyzed for yield, selectivity, and cost, and revised reaction conditions are generated to further optimize the set of objectives of yield, selectivity, and cost.

Although the embodiments of FIG. 4 describe using different temperatures to drive the reactions, embodiments are not so limited and can include use of the same temperature and/or use of different energy sources, such as microwaves or light.

Figure 5:
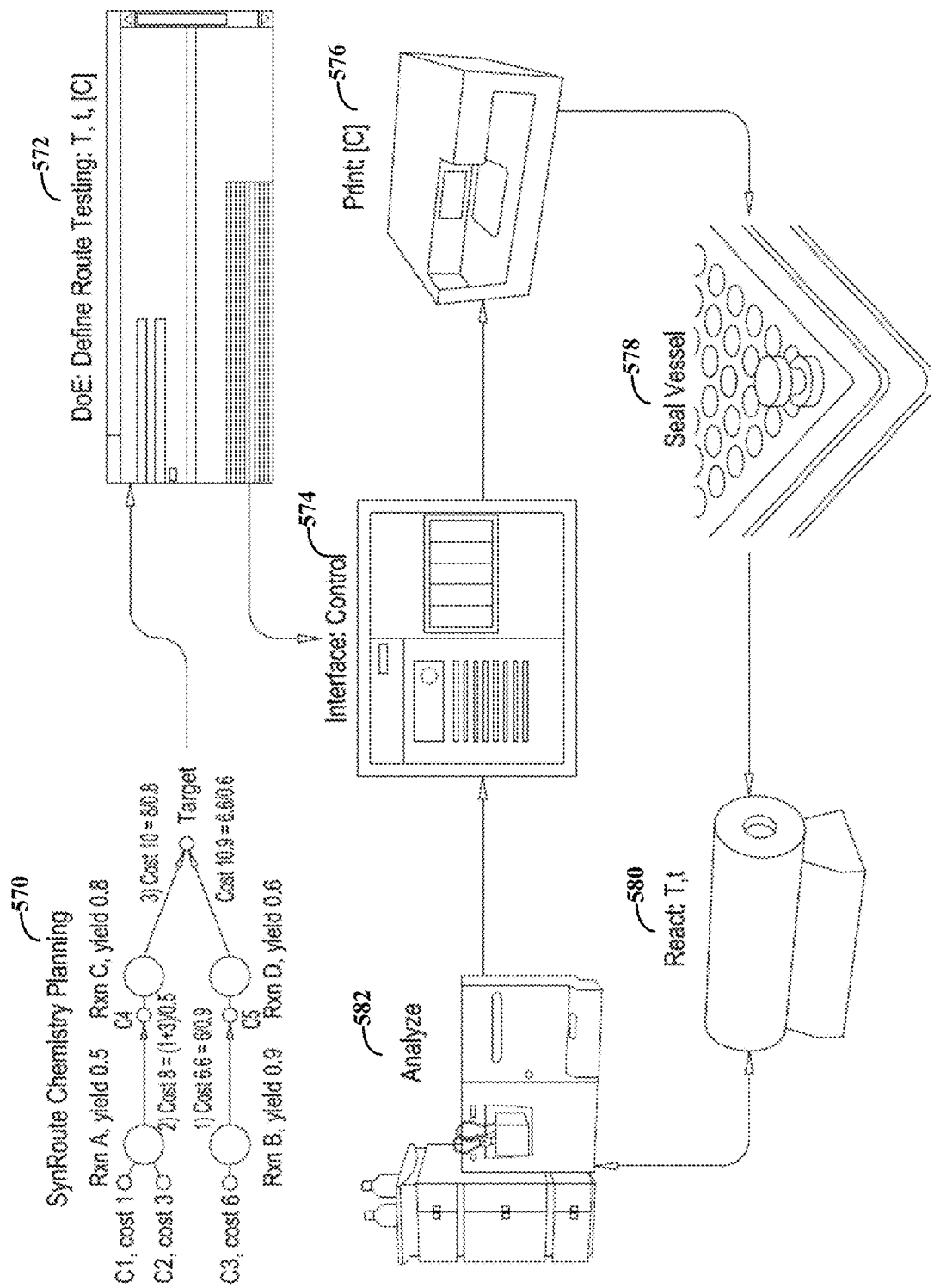
FIG. 5 illustrates example components of an apparatus used for performing reaction screening and optimization, in accordance with various embodiments.

FIG. 5 illustrates example components of an apparatus used for performing reaction screening and optimization, in accordance with various embodiments. More specifically, FIG. 5 illustrates components involved in the process as described by FIG. 4. As illustrated, to define the experimental design parameters, chemistry planning is performed, at 570. In specific embodiments, the chemistry planning can include computation generation of chemical synthesis routes and methods that automates the process from target molecule through development of experimental methods. The chemistry planning can consider anticipated yields and costs.

In more specific embodiments, the chemistry planning can include using another unified system used that operates through a graphical user interface (GUI). The technique can be used to generate synthetic chemistry strategies and procedures for new chemical entities (NCEs) or new synthetic procedures for known compounds with less expensive reagents and/or more efficient synthetic transformations. The methodology can include searching a computation network of synthetic chemistry reactions for optimal routes using a scoring function that accounts for chemical transformations and process variables; generation of new hypothesized chemical reactions using a reaction pattern template and machine learning classifiers to assess reaction success or yield, developing new computation representations of reactions that are suitable for machine learning, and automated development of experimental methods for computationally-generated reaction. The chemistry planning is used to define the experimental design parameters which are input to an apparatus that performs reaction screening and optimization for reaction conditions of a target end product, such as those apparatus as described above. For example, and as further described below, the experimental design parameters are input to an apparatus used to explore potential synthetic routes and identify an optimum route having particular reaction conditions among those provided in the experimental design parameters and which can optionally be used to provide feedback control for regressive reaction design and optimization.

As provided above, based on the chemistry planning, the experimental design parameters are defined at 572. As previous described, the experimental design parameters include a set of synthetic routes for reaching a target end product according to a plurality of varied reaction conditions. Example varied reaction conditions include temperature or other energy sources, time, and concentration of reagents, although embodiments are not so limited. The experimental design parameters are input or otherwise provided to the control circuitry of the apparatus which is used to control the dispersal of reagents, and to drive the reactions.

In specific embodiments, the control circuitry provides the set of reaction mixtures (e.g., different concentrations of reagents) to the dispensing subsystem via an interface 574. At 576, the dispensing subsystem disperses the reaction mixtures according to the experimental design parameters. The reaction vessels which contain the reaction mixtures are sealed, at 578, such as via automation subsystem, and moved to the at least one reactor module, at 580. The at least one reactor module exposes the reaction vessels to one or temperatures (or other energy sources) for one or more periods of time according to the experimental design parameters. The resulting compositions of the reaction mixtures contained within the reaction vessels are analyzed via an analysis subsystem to identify optimum reaction conditions from the plurality of varied reaction conditions, at 582. Control circuitry can, optionally, use the analysis as further feedback control. As described above, the analyzed compositions can be used to automatically design one or more additional tests to run to further optimize the reaction conditions for the target end product.

Figure 6A:
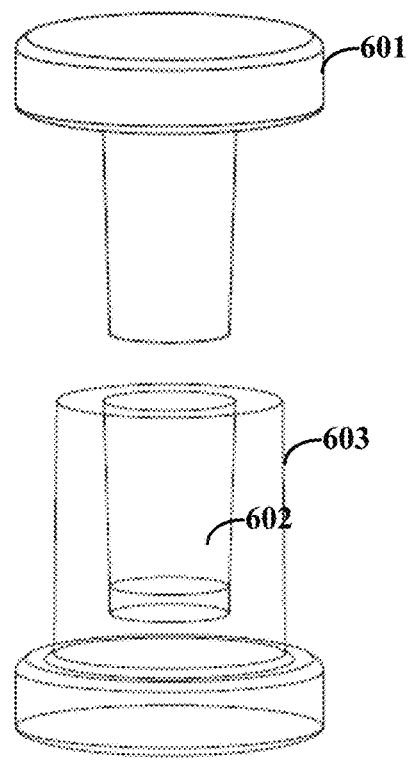
FIGS. 6A-6F illustrate examples of reaction vessels, in accordance with various embodiments.
Figure 6B:
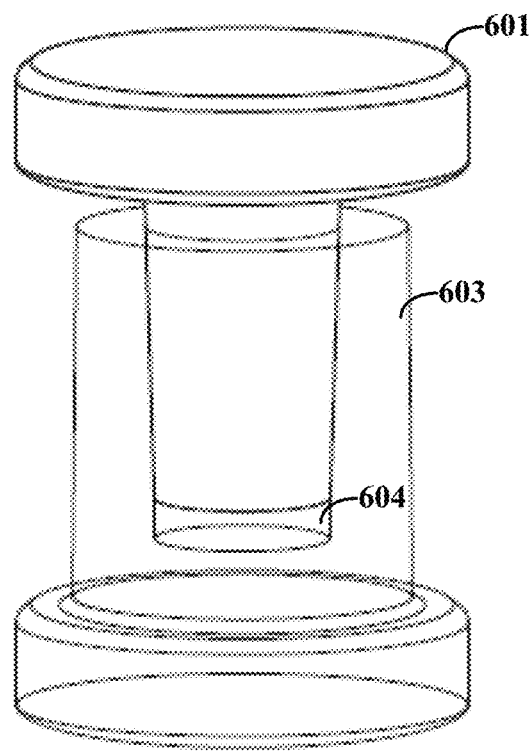
Figure 6C:
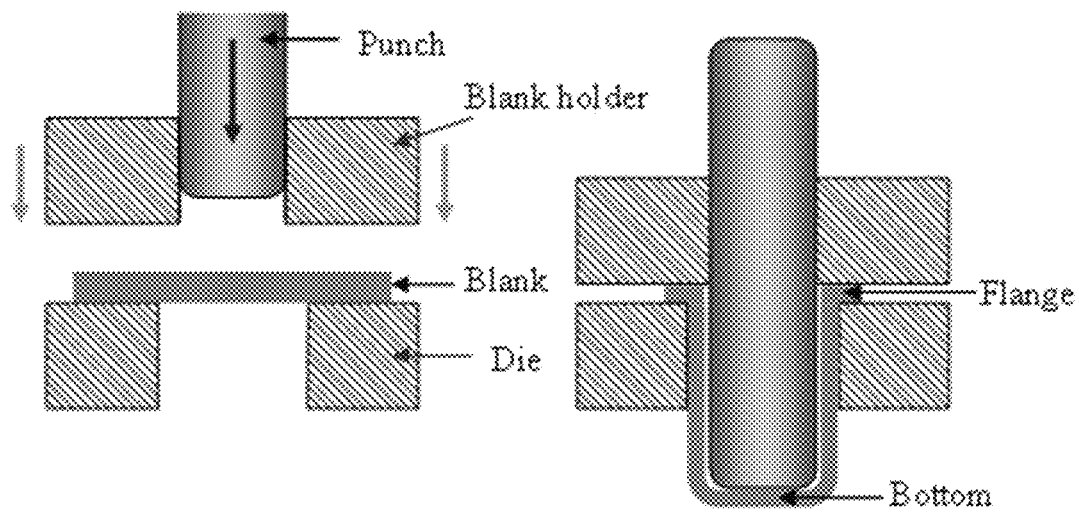

FIGS. 6A-6F illustrate examples of reaction vessels, in accordance with various embodiments. More specifically, FIGS. 6A-6B illustrates an example reaction vessel 603 that is tapered and has a cap 601. The reaction vessel 603 has a cavity 602 that can hold a reaction mixture. The reaction vessel 603, when capped, provides a volume for the reaction mixture of 20 uL (e.g., cavity 604 illustrated by FIG. 6B), however, embodiments are not so limited. FIG. 6C illustrates an example method of forming the vessels, which may be performed by the automation subsystem, in some more specific embodiments. As illustrated a punch is used to create the tapered reaction vessel from a blank material.

Figure 6D:
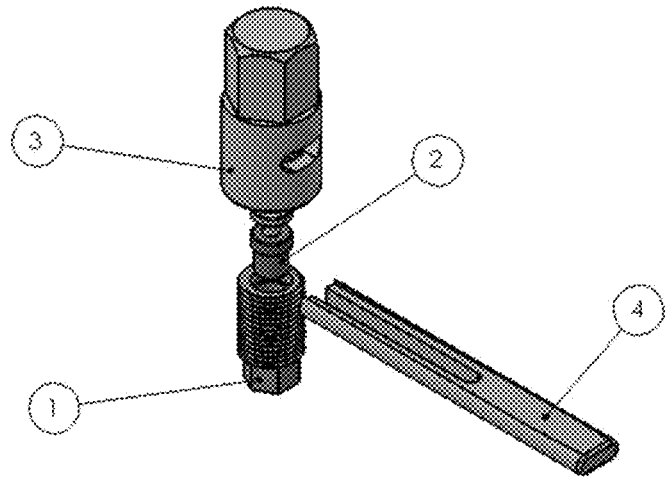
Figure 6E:
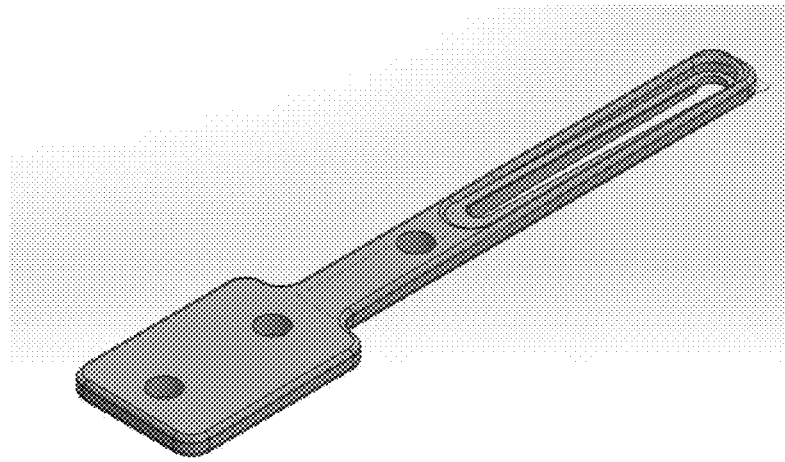

FIGS. 6D-6E illustrate example tools for attaching or detaching caps to reaction vessels, in accordance with various embodiments. In some specific embodiments, the reaction vessels can include Hastelloy C276 vessels prototyped (5 mm opening). As illustrated by FIG. 6D, the reaction vessels can be sealed via pressure and/or sealing. The reactions vessels can be formed of a variety of material, such as glass, polyether ether ketone (PEEK), Perfluoroalkoxy (PFA), SS, SS with Dursan coating. The reaction vessels can be unsealed, such as by the automation subsystem using the tool illustrated by FIG. 6E.

In a number of specific embodiments, the reaction vessels are vials that are self-sealing or otherwise sealed by the automation subsystem. The vials can be made of PEEK and can be computer numerical control (CNC) machined, such as to 0.0005" tolerances. In other embodiments, the vials made of PEEK can be produced via injection mold and made to scale with the appropriate tolerance for mating and sealing. The reaction vessels can be designed to fit within a standard 96 well plate assay or for other types of formats (e.g., 384 wells). The interior of the vial is produced to allow for a volume of reagents, as an example 25 ul. with twice (e.g., 2×) headspace (e.g., a total volume of 50 uL) once sealed. However, embodiments are not so limited and the vials can be any volume by removing more material from the cap or interior of the vessel.

The vial seal can include two mating surfaces with (low) surface roughness, such that when an appropriate force is applied to the cap (e.g., 10 lbf), the cap sufficiently seals the reagents into the vial (e.g., interference seal). The surface area of the mating surface, surface roughness, modulus of the material, and machining tolerances can all play a role into forming a high pressure seal. The seal between the cap and vial, in some specific embodiments, is designed to hold 300 pound-force per square inch (psi) of pressure.

Removing the cap from the vial can involve a wedge force between two flanges, such as via a tool as illustrated by 6E. This allows for the automation subsystem to remove the cap, without the use of a screw rotation or crimp tool. In number of specific embodiments, the vial may have a puncturable location, either top, side or bottom, to facilitate product retrieval and analysis (e.g., LCMS) by unsealing the reaction vessels via puncturing the seal.

Figure 6F:
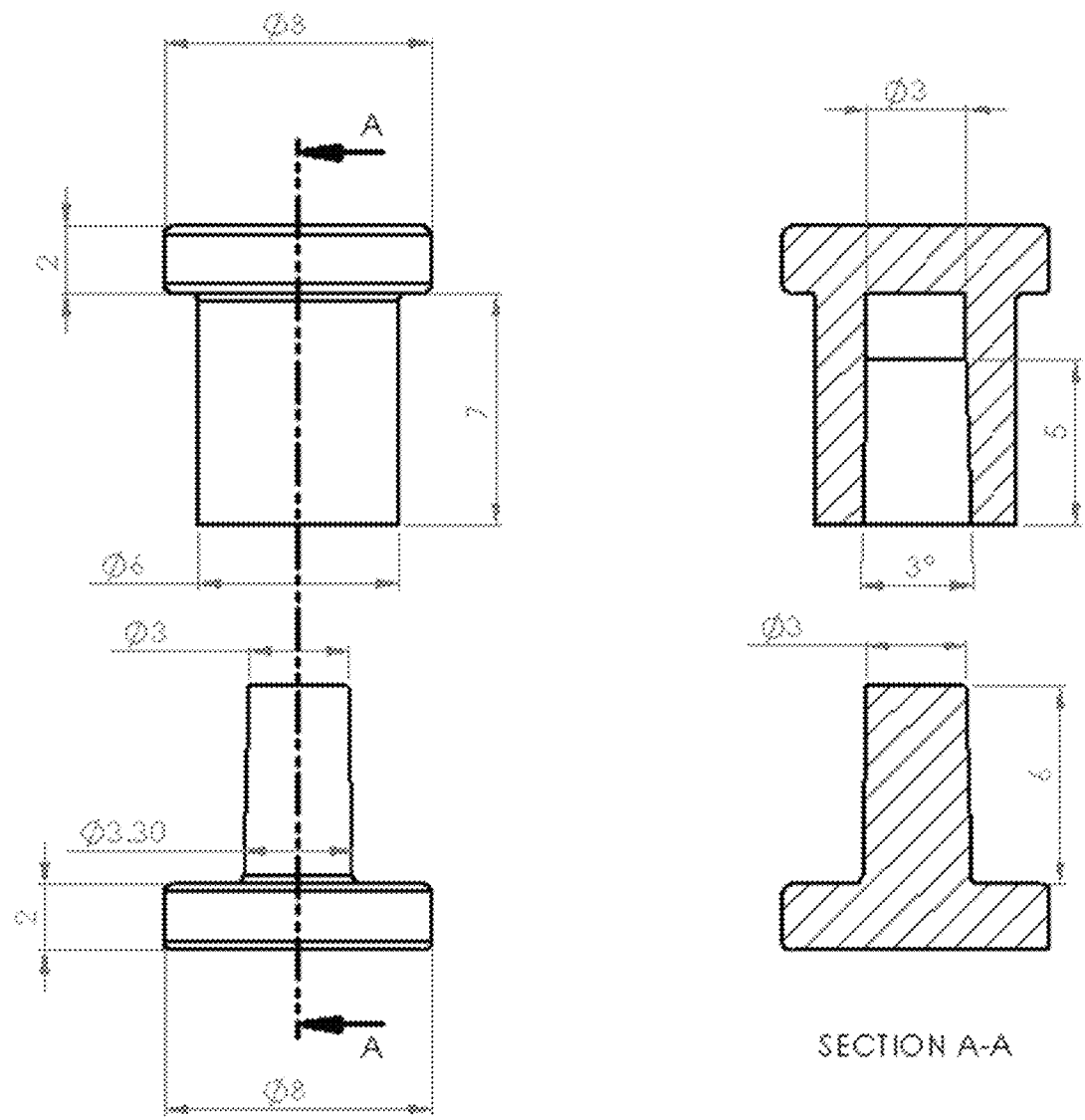

FIG. 6F illustrates an example reaction vessel with dimensions, in accordance with various embodiments. Although embodiments are not so limited. In such embodiments, the volume of chamber of the reaction vessel is $(3/2)^2 (3.1415) 2.829 = 20$ mm3. The reaction vessels, in such example embodiments, can be sealed with 300 psi, however, embodiments are not so limited.

As may be appreciated, embodiments are not limited to the reaction vessels as illustrated by 6A-6F. For example, the reaction vessels can include glass (or plastic) vials with an aluminum (or other material) cap that are sealed using a crimp tool. In other embodiments, the reaction vessels are the wells of a substrate (e.g., well plate assay), such as illustrated by FIG. 7A-7B.

Figure 7A:
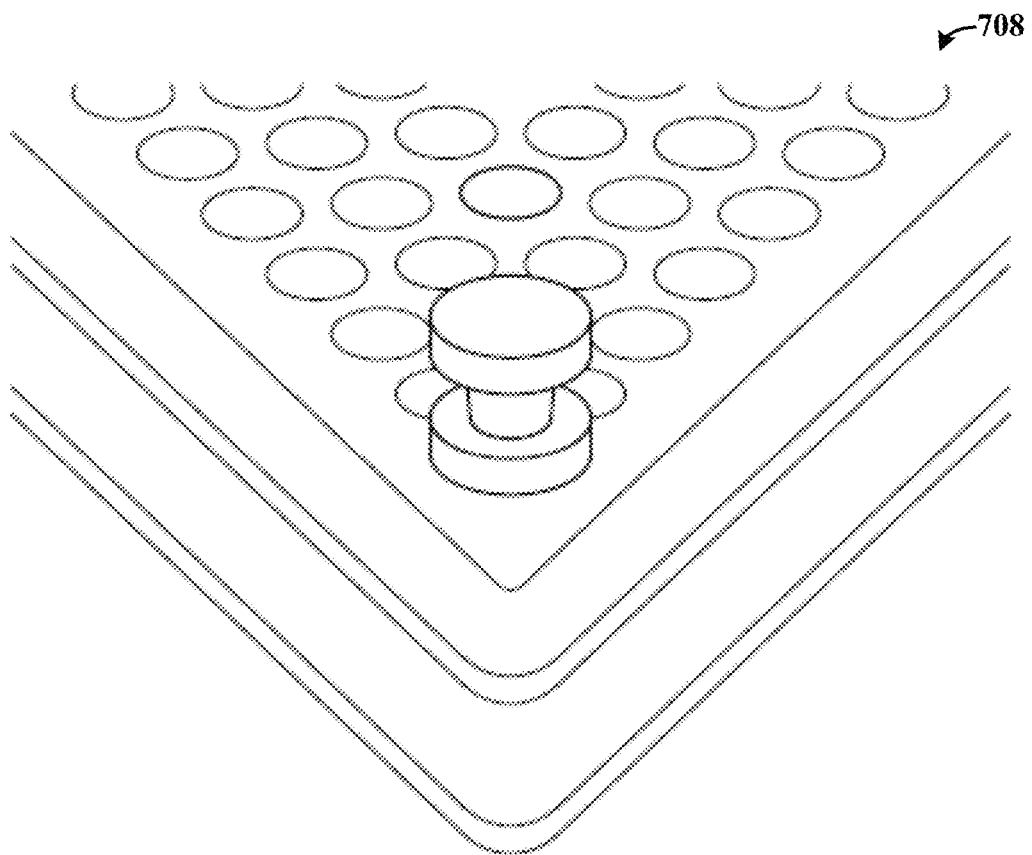
FIGS. 7A-7B illustrate example substrates, in accordance with various embodiments.
Figure 7B:
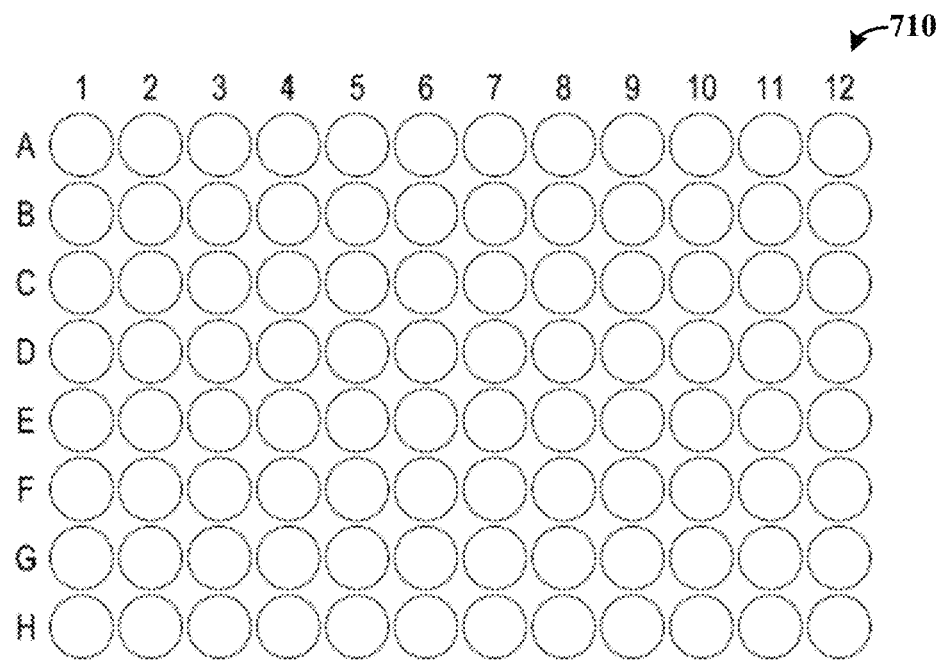

FIGS. 7A-7B illustrate example substrates, in accordance with various embodiments. For example, FIG. 7A illustrates an example substrate 708 having cavities (e.g., holes) configured to hold an individual reaction vessel. FIG. 7B illustrates an example substrate 710 having wells, such as a microtiter plate, as previously discussed.

Figure 8:
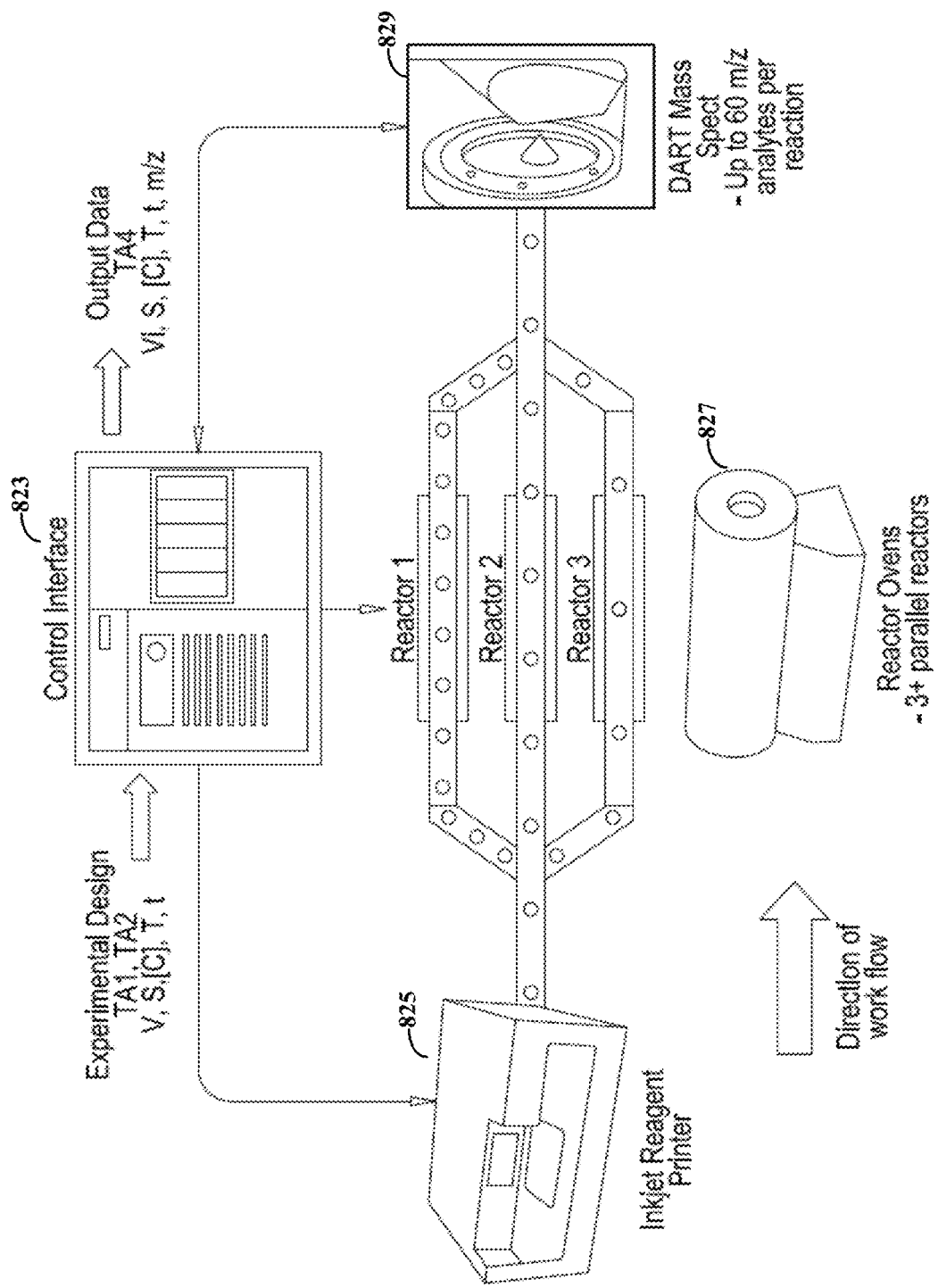
FIG. 8 illustrates a specific example of using an apparatus, in accordance with various embodiments.

FIG. 8 illustrates a specific example of using an apparatus, in accordance with various embodiments. The apparatus includes the previously described control circuitry that provides a control interface 823, at least one reactor module 827, an automation subsystem, an analysis subsystem (e.g., DART-MS 829), and a dispensing subsystem (e.g., inkjet printer 825). The specific apparatus illustrated has a DART-MS 829, an inkjet printer 825. and a plurality of reactor modules that operate in parallel. Each of the reactor modules can expose respective reaction mixtures to a different temperature (or other energy source), for a total of three different temperatures, although embodiments are not so limited. The control circuitry can provide feedback control in a threshold period of time, which can be near-instantaneous. As previously described, the compositions can be analyzed for a particular objective or set of objectives, such as product yield and cost, and feedback is used to further optimize the particular objective or set of objectives. As a specific example illustrated by FIG. 8, the compositions are analyzed for yield, purity, and cost, and the revised reaction conditions are generated to further optimize the one or more of the set of objectives. In the specific embodiment, the compositions are analyzed for viscosity, purity, selectivity, and m/z values.

Although the embodiment of FIG. 8 illustrates DART-MS and parallel reactor modules, embodiments are not so limited. For example, in some embodiments, a reel of tape print substrate is fed through an array of an inkjet printer. Reagents are printed as directed by the control circuitry in spots or wells of the substrate. The tape is moved through the at least one reactor module to drive the reaction (e.g., expose to a temperature), and then moved to the analysis subsystem. Other embodiments can include LC-MS analysis, reactor modules having different zones, other types of dispensing subsystems, and various additional automation circuitry and hardware.

Figure 9A:
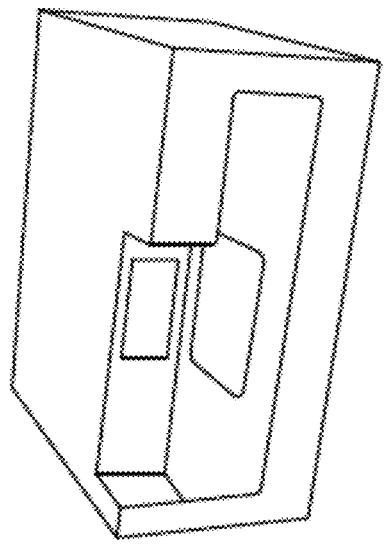
FIGS. 9A-9C illustrate an example of a dispensing subsystem, in accordance with various embodiments.
Figure 9B:
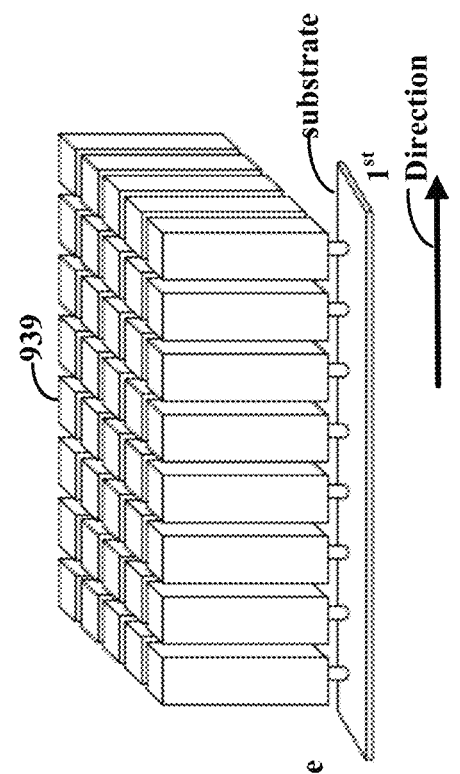
Figure 9C:
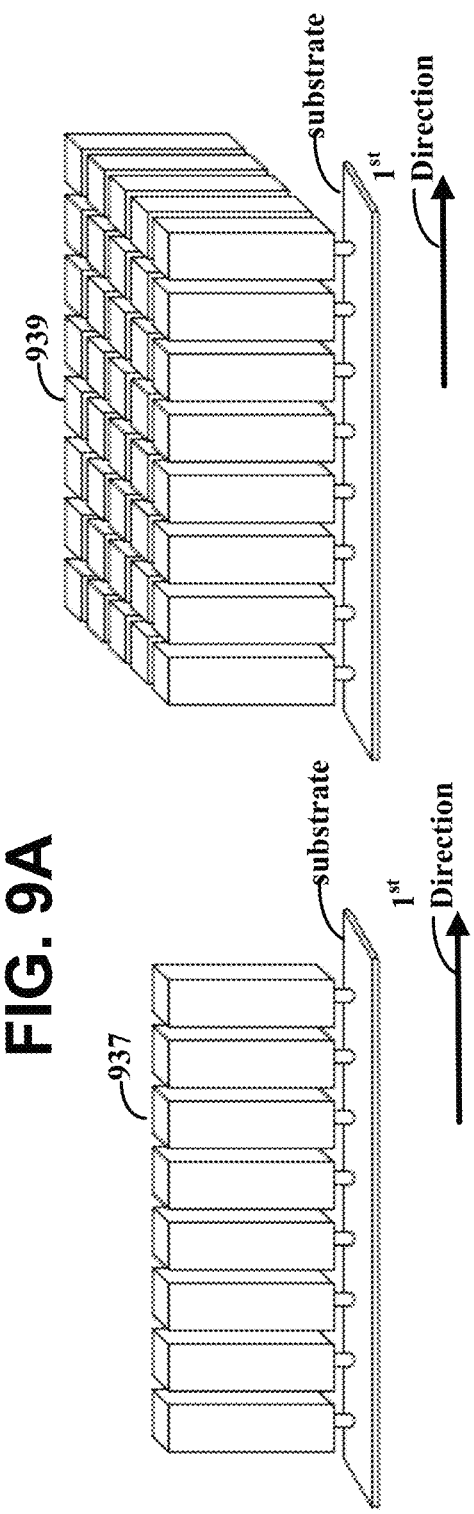

FIGS. 9A-9C illustrate an example of a dispensing subsystem, in accordance with various embodiments. FIG. 9A illustrates an example of an inkjet subsystem 933. FIG. 9B illustrates an example of a substrate that is moved in a first direction for reagent delivery by an 8-channel printer head 937. FIG. 9C illustrates an example of a 96-channel printer head 939 and movement of a substrate in a first direction for reagent delivery. The substrates illustrated by FIGS. 9B-9C can include the plurality of reaction vessels, such as wells and/or vials, and is moved by a stage of the dispensing subsystem (and/or the automation subsystem, in some embodiments).

Figure 10A:
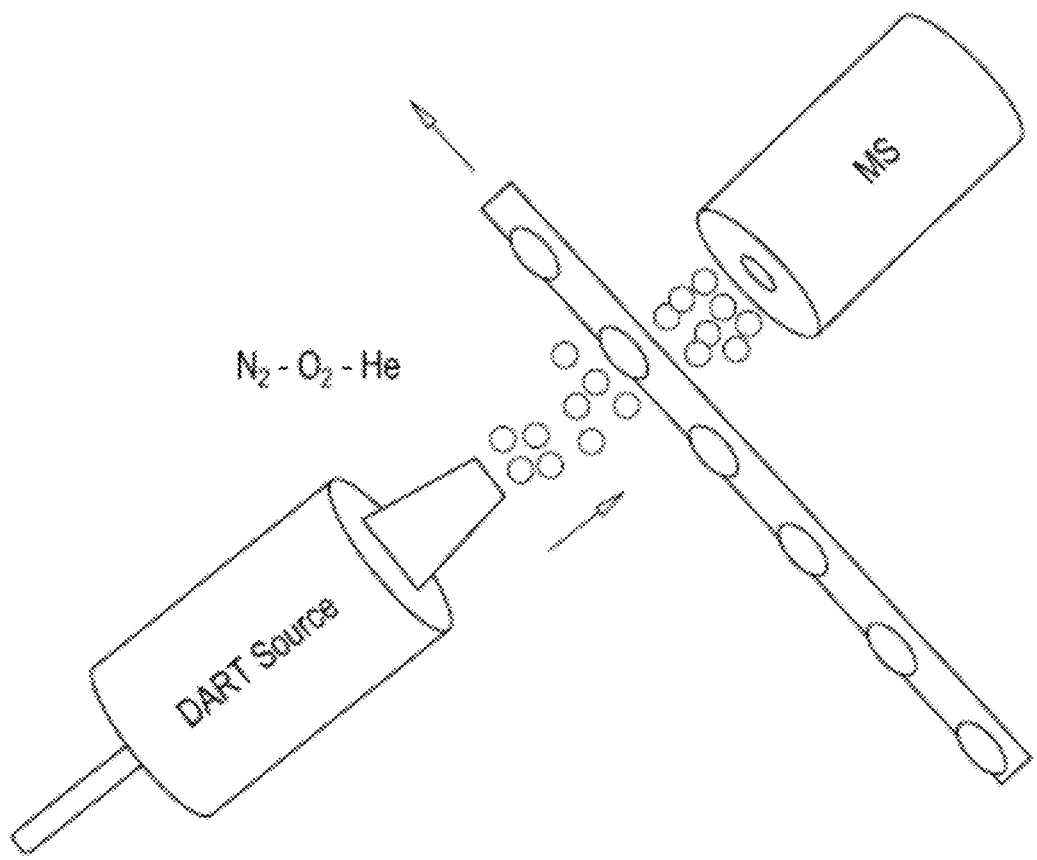
FIGS. 10A-10B illustrate example analyzer subsystems, in accordance with various embodiments.
Figure 10B:
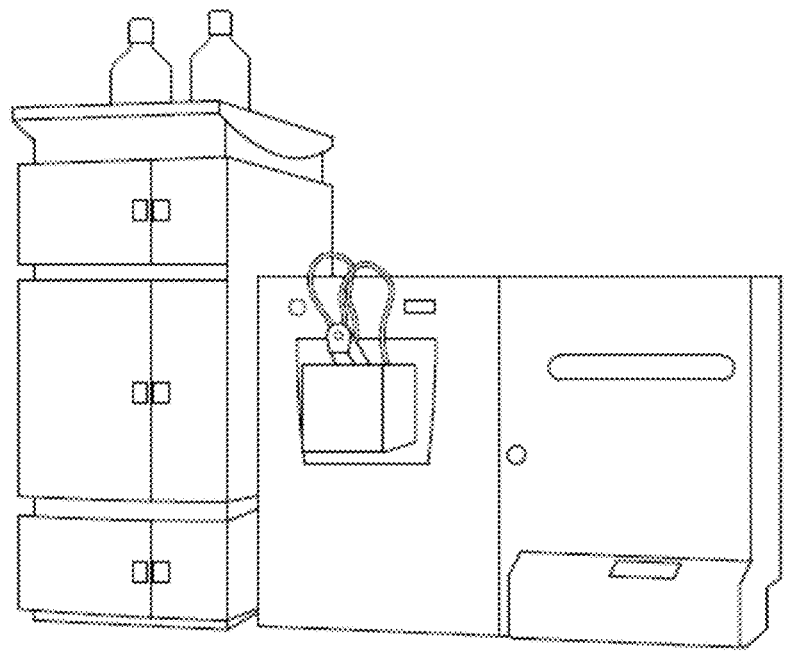

FIGS. 10A-10B illustrate example analyzer subsystems, in accordance with various embodiments. For example, FIG. 10A illustrates an example of a DART-MS. As would be appreciated, DART-MS operates by use of an ion source in mass spectrometry. The DART ionization source provides a beam of gas directed toward each reaction mixture sequentially and carries a sample of each reaction mixture back to the DART-MS. e.g., to an inlet of the mass spectrometer (MS). The reaction vessels can be passed in front of the DART ionization source under atmospheric conditions, such as via movement of the reaction mixtures (e.g., reaction vessels individually or a substrate containing a plurality of vessels) by the automation subsystem onto a conveyor and/or via the movable arm of the automation subsystem itself. The MS analyzes compositions, e.g., reactants, side products, end products, and byproducts, of the reaction mixtures based on the ions generated therefrom. DART-MS has a rapid response (1 to 3 samples/second) and high sensitivity (such as parts per billion (ppb)). In various embodiments, the ion beam can be provided toward the top of the reaction vessels, as previously described.

Direct real-time reaction analysis can allow machine learning based on the DOE information for iterative optimization of reaction steps. The analysis of the compositions can be used for feedback control by the control circuitry interpreting analytical data and incorporates multiple reaction data points to design the next reaction combination to optimize the synthesis step.

FIG. 10B illustrates an example of a LC-MS. As may be appreciated, LC-MS includes an analytical chemistry technique that combines the physical separation capabilities of liquid chromatography (or HPLC) with the mass analysis capabilities of mass spectrometry.

Embodiments in accordance with the present disclosure include a variety of apparatuses and methods of using the apparatuses for integrated compound synthesis and function screening. Such embodiments can be used to discover compounds with novel functions (e.g., protein inhibition, catalytic activity, etc.) in a continuous process and to rapidly synthesize test compounds (e.g., end products), print reactions that test the compounds for activity (e.g., the objectives), and quantitate the activity of each compounds by analysis of the product mixture. Integration and automation of the synthesis and screening process on single high-throughput platform allows for progression through multiple generations of compound testing and refinement, e.g., feedback control, for convergence on specified objectives.

MORE DETAILED/EXPERIMENTAL EMBODIMENTS

Various experimental embodiments can be performed and which illustrate analysis (and printing) of reaction mixtures at a speed on an order of (e.g., up to or more) one reaction per second. FIGS. 1A-1B illustrate an example experimental embodiment, in accordance with various embodiments. The experimental embodiment(s) can be used to validate delivery of solutions and can include calibrating the delivery of solutions by the dispensing subsystem using standard analytic practices.

Figure 11A:
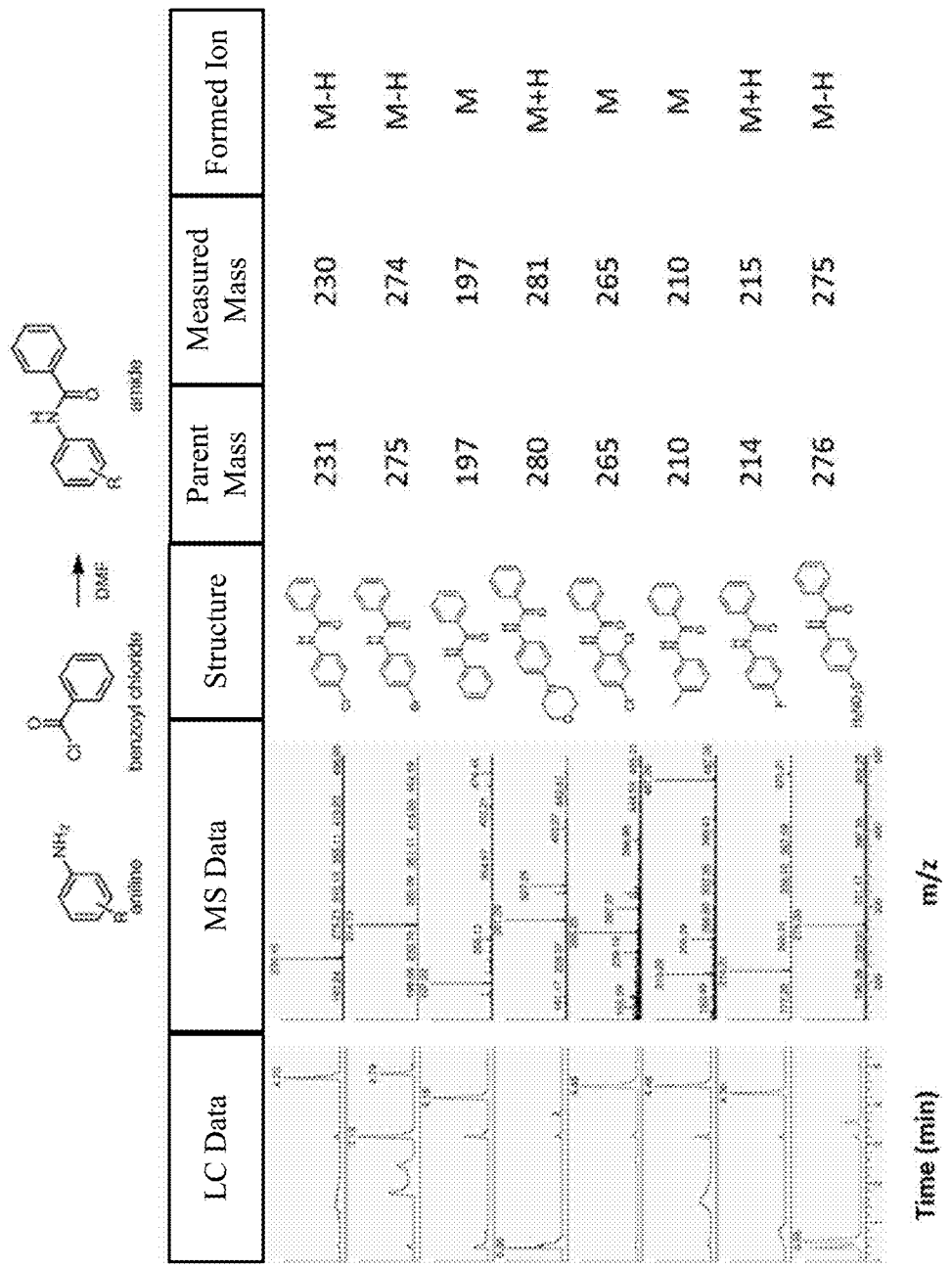
FIGS. 11A-11B illustrate an example experimental embodiment, in accordance with various embodiments.

More specifically, FIG. 11A shows results of a demonstration of screening of amides from eight different amines and one acid chloride using an apparatus in accordance with the present disclosure. As illustrated, the end product (e.g., target) is illustrated in each case, demonstrating the capability of printing for reactivity screening. The inkjet printer used includes the HP D300e, however, embodiments are not so limited.

A number of specific embodiments can include the use of an experimental design parameter interface that provides the experimental design parameters. The experimental design parameters can include a list of reaction conditions and values for each reaction condition. The example includes compounds and solvents, stoichiometry range, time and temperature conditions, and normalized values for dispensing (e.g., calibration), although embodiments are not so limited. From the reaction conditions, a plurality of sets of reaction conditions are generated as the experimental design parameters.

In a specific experimental embodiment, the above-described experimental design parameter interface is used to generate experimental design parameters for a fluconazole experiment. The experiment can include dispensing 50 mM chloroacetophenone (e.g., illustrated as A in FIG. 11B) and 200 mM triazole (e.g., illustrated as B in FIG. 11B) and reacting the reagents to generate fluconazole (e.g., illustrated as C in FIG. 11B). The reaction conditions include temperature, time, and concentration. The different values of the reaction conditions can include:

Conditions
T: 25 C, 50 C, 70 C, 90 C, 130 C, 170 C
t: 15 min, 127.5 min, 240 min
B=1.4*A, 7.8*A, 14.1*A
A: 5 mL into 34 µL total.

Figure 11B:
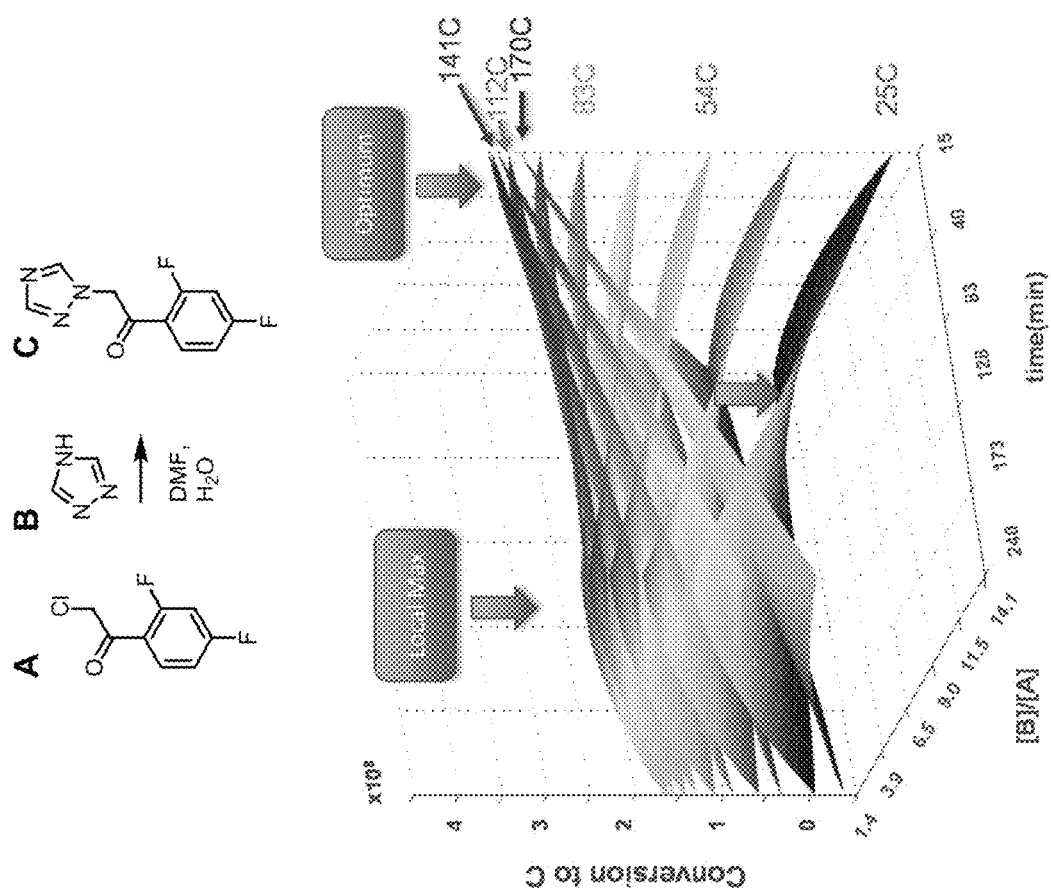

FIG. 11B illustrates example results of the experiment for the preparation of a synthetic intermediate in the preparation of fluconazole, in accordance with various embodiments. As illustrated, the graph includes a regression of the three reaction conditions (time, concentration, and temperature) based on the different values of the reaction conditions as optimized for the target end product (e.g., conversion to compound C). The apparatus identifies the optimized reaction conditions (e.g., 15 minutes, 141 C. B=14*A), such as in a time of one to two days. As may be appreciated, embodiments are not limited to the above described experimental embodiment and can include reaction screening and optimization for a variety of reaction conditions and objectives.

Various embodiments are implemented in accordance with embodiments in U.S. Provisional Application (62/527, 365), entitled "SynJet: Inkjet Printing to Enable Rapid Chemical Synthesis," filed Jun. 30, 2017, which is fully incorporated herein by reference. For instance, the embodiments described therein may be combined in varying degrees (including wholly) with the embodiments described above. As a specific example, which is described above in connection with FIG. 1. reaction screening and optimization, as described by various embodiments herein and illustrated at least by FIG. 1, can be implemented as the apparatus as described and illustrated by FIG. 1 of U.S. Provisional Application, 62/527,365. Embodiments discussed in the U.S. Provisional Application are not intended, in any way, to be limiting to the overall technical disclosure, or to any part of the claimed invention unless specifically noted.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions (e.g., reference numerals 102, 108 and 228 of FIG. 1 and FIG. 2A depict a block/module as described herein). Such circuits or circuitry are used together with other elements to exemplify how certain embodiments may be carried out in the form or structures, steps, functions, operations, activities, etc. For example, in certain of the above-discussed embodiments, one or more modules are discrete logic circuits or programmable logic circuits configured and arranged for implementing these operations/activities, as may be carried out in the approaches shown in FIG. 1. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIG. 4 is used by the programmable circuit to perform the related steps, functions, operations, activities. etc. Depending on the application, the instructions (and/or configuration data) can be configured for implementation in logic circuitry, with the instructions (whether characterized in the form of object code, firmware or software) stored in and accessible from a memory (circuit).

Various embodiments described above, and discussed provisional application may be implemented together and/or in other manners. One or more of the items depicted in the present disclosure and in the underlying provisional application can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. An apparatus for reaction screening and optimization, comprising:
   a substrate including a plurality of reaction vessels;
   a dispensing subsystem including a dispenser configured and arranged to deliver reagents to the plurality of reaction vessels for a plurality of reaction mixtures of the reagents in accordance with experimental design parameters, the experimental design parameters including a set of synthetic routes each designed to reach a single target end product according to a plurality of reaction conditions for a plurality of reactions, wherein the plurality of reaction conditions each vary for the plurality of reactions by a plurality of values and include at least one of different reagents and different reagent concentrations, and wherein the single target end product is known and is the same for each of the set of synthetic routes;
   at least one reactor module configured and arranged to output energy to drive the plurality of reactions of the reaction mixtures within the plurality of reaction vessels in parallel and at a temperature in accordance with the experimental design parameters to form compositions within the plurality of reaction vessels;
   an analysis subsystem configured and arranged to analyze the compositions while contained within the plurality of reaction vessels and after the reactions have begun, the analysis being at a speed on an order of one reaction per second;
   an automation subsystem configured and arranged to selectively move the plurality of reaction vessels from a location proximal to the dispensing subsystem to the at least one reactor module and from the at least one reactor module to a location proximal to the analysis subsystem based on the experimental design parameters; and
   control circuitry configured and arranged to provide the experimental design parameters to the dispensing subsystem and the automation subsystem for feedback control of the plurality of reactions and to identify optimum reaction conditions for synthetically forming the single target end product based on the analysis of the compositions received from the analysis subsystem, the optimum reaction conditions including a set of reaction conditions to synthetically form the single target end product as optimized for an objective, the set of reaction conditions including select values for each of the plurality of reaction conditions as defined by the experimental design parameters.

2. The apparatus of claim 1, wherein:
   the control circuitry is configured and arranged to provide the feedback control by adjusting the plurality of reaction conditions for a plurality of additional reactions to synthetically form the single target end product based upon comparing previous reaction results with optimal reaction product yields stored in the analysis subsystem and providing the adjusted plurality of reaction conditions as revised experimental design parameters to the dispensing subsystem and the automation subsystem, wherein the speed of an order of one reaction per second includes a speed of up to one reaction per second; and
   wherein the analysis subsystem is configured and arranged to analyze the compositions by comparing the compositions contained within the plurality of reaction vessels to a target composition, the target composition being selected from the single target end product and an intermediate of the single target end product and wherein the objective is selected from the group consisting of: yield, purity, cost, and a combination thereof.

3. The apparatus of claim 1, wherein the plurality of reaction conditions further include at least one of exposure to different temperatures and for different periods of time to synthetically form the single target end product, the reaction vessels are independently selectable from one another, and the automation subsystem is further configured and arranged to selectively and individually move a first of the plurality of reaction vessels to a first location associated with the at least one reactor module, selectively and individually move a second of the plurality of reaction vessels to a second location associated with the at least one reactor module, and individually move each of the first and second of the plurality of reaction vessels to a location proximal to the analysis subsystem upon completion of the respective reactions, and the optimum reaction conditions including the set of reaction conditions include values for:
   at least one of reagents and reagent concentrations; and
   at least one of temperature and period of time.

4. The apparatus of claim 1, wherein:
   the dispensing subsystem includes the dispenser selected from the group consisting of: an inkjet printer, a liquid dispenser, and a combination thereof; and
   the analysis subsystem includes an analyzer selected from the group consisting of: a liquid chromatography-mass spectrometer (LC-MS), a direct analysis in real time (DART)-mass spectrometer (MS), a spectroscopic imager, and a combination thereof.

5. The apparatus of claim 1, wherein the at least one reactor module includes an energy emitter configured and arranged to provide an energy output toward the plurality of reaction vessels and thereby drive the plurality of reactions, and wherein the objective is selected from the group consisting of: yield of the single target end product, selectivity of the single target end product, purity of the single target end product, time to form the single target end product, cost to form the single target end product, and a combination thereof.

6. The apparatus of claim 1, wherein the analysis subsystem includes a direct analysis in real time (DART)-mass spectrometer (MS) configured and arranged to provide a beam of gas directed toward each reaction mixture sequentially and configured to carry a sampling of each reaction mixture to the DART-MS.

7. The apparatus of claim 1, wherein the automation subsystem is further configured and arranged to move the reaction mixtures from the at least one reactor module to a location proximal to the analysis subsystem, and wherein the analysis subsystem is configured and arranged to emit an analysis beam emitted toward each of the plurality of reaction vessels that is approximately parallel to a top portion of the reaction vessels.

8. The apparatus of claim 7, further including sensor circuitry configured and arranged to detect an audio frequency signal associated with the analysis beam used to sample each reaction mixture of the plurality and provide a signal indicative of the audio frequency signal to the control circuitry in response, wherein the control circuitry is further configured and arranged to compare the audio frequency signal to a threshold audio frequency and therefrom verify whether analysis is occurring.

9. The apparatus of claim 1, wherein:
the automation subsystem includes:
   a first distribution chamber configured and arranged to contain the plurality of reaction vessels;
   a second distribution chamber configured and arranged to contain a plurality of caps for the plurality of reaction vessels; and
   at least one movable arm configured and arranged with the first distribution chamber and the second distribution chamber to distribute the plurality of reaction vessels and the plurality of caps; and
the control circuitry and the automation subsystem are further configured and arranged to seal each of the plurality of reaction vessels using the plurality of caps and application of pressure and prior to the plurality of reactions being driven within the reaction vessels, and to unseal each of the plurality of reaction vessels mid-reaction to introduce other reagents, to sample the reaction mixture, or prior to the analysis of at least one of the compositions.

10. The apparatus of claim 1, wherein the at least one reactor module includes a plurality of reactor modules configured and arranged to drive the plurality of reactions in parallel and at a plurality of different temperatures, and each of the reactor modules includes a thermal energy emitter configured and arranged to provide thermal energy toward at least a portion of the plurality of reaction mixtures.

11. A method comprising:
providing a plurality of experimental design parameters that include a set of synthetic routes each designed to reach a single target end product according to a plurality of reaction conditions for a plurality of reactions, via control circuitry, to a dispensing subsystem and an automation subsystem for controlling a plurality of reactions of reagents within a plurality of reaction vessels, wherein the single target end product is known and is the same for each of the set of synthetic routes and wherein the plurality of reaction conditions each vary with a plurality of values and include:
   different temperatures, different periods of time, and at least one of different reagents and different reagent concentrations;
delivering different amounts of the reagents to respective reaction vessels of the plurality of reaction vessels by the dispensing subsystem including a liquid dispenser and according to the experimental design parameters to form reaction mixtures of the different amounts of the reagents contained within the plurality of reaction vessels;
selectively moving, by the automation subsystem, the plurality of reaction vessels from a location proximal to the dispensing subsystem to at least one reactor module;
driving, by the at least one reactor module, the plurality of reactions of the reaction mixtures within the plurality of reaction vessels in parallel to form compositions within the plurality of reaction vessels, the plurality of reactions being driven in accordance with the plurality of reaction conditions, including exposure to the different temperatures and the different periods of time, as defined by the experimental design parameters;
selectively moving, by the automation subsystem, the plurality of reaction vessels from the at least one reactor module to a location proximal to an analysis subsystem;
analyzing, by analysis subsystem, the compositions while contained within the plurality of reaction vessels at a speed on an order of one reaction per second; and
identifying, by the control circuitry, optimum reaction conditions for synthetically forming the single target end product based on the analysis of the compositions received from the analysis subsystem, the optimum reaction conditions including a set of reaction conditions to synthetically form the single target end product as optimized for an objective, and the set of reaction conditions including select values for each of the plurality of reaction conditions as defined by the experimental design parameters.

12. The method of claim 11, further including selectively moving the plurality of reaction vessels to a location proximal to an analysis subsystem responsive to the plurality of reactions being driven to completion, wherein the compositions are analyzed by the analysis subsystem by comparing the compositions contained within the plurality of reaction vessels to a target composition, the target composition is the single target end product or an intermediate of the single target end product.

13. The method of claim 11, wherein delivering the different amounts of reagents using the dispensing subsystem further includes providing a plurality of reaction mixtures having different concentrations of reagents to different reaction vessels of the plurality of reaction vessels according to the experimental design parameters.

14. The method of claim 11, wherein identifying the optimum reaction conditions for the single target end product further includes identifying optimized experimental design parameters selected from the group consisting of: reagents, concentration of reagents, temperature, time, stoichiometry, and a combination thereof.

15. The method of claim 11, further including providing, based on the analysis of the compositions, adjusted reaction conditions for a plurality of additional reactions designed to reach revised optimum reaction conditions for synthetically forming the single target end product using machine learning, and providing the adjusted reaction conditions as revised experimental design parameters to the dispensing subsystem and the automation subsystem.

16. The method of claim 15, wherein identifying the revised optimum reaction conditions for the single target end product includes using the revised experimental design parameters to run an additional test and further optimizing reaction conditions for synthetically forming the single target end product from an analysis of the compositions therefrom.

17. The method of claim 11, further including providing a beam of gas directed toward each of the plurality of reaction vessels, wherein the beam of gas is directed at an angle that is approximately parallel to a top portion of the plurality of reaction vessels and the gas beam carries a sampling of a respective reaction mixture to an analysis subsystem for analyzing the compositions contained in the reaction vessels based on ions generated therefrom.

18. An apparatus for reaction screening and optimization, comprising:
 a plurality of reaction vessels that are individually selectable and separable, wherein the plurality of reaction vessels include reagents contained therein according to experimental design parameters for a plurality of reaction mixtures, the experimental design parameters including a set of synthetic routes each designed to reach a single target end product according to a plurality of reaction conditions for a plurality of reactions, wherein the plurality of reaction conditions each vary with a plurality of values and include exposure to different temperatures, different periods of time, and at least one of different reagents and different reagent concentrations, and wherein the single target end product is known and is the same for each of the set of synthetic routes;
 at least one reactor module configured and arranged to output energy to drive the plurality of reactions of the plurality of reaction mixtures within the plurality of reaction vessels in accordance with the plurality of reaction conditions and in parallel to form compositions within the plurality of reaction vessels, including the exposure to the different temperatures for the different periods of time; and
 an analysis subsystem configured and arranged to analyze the compositions while contained within the plurality of reaction vessels and after the reactions have begun and at any time during a set of reaction times by providing an analysis beam selectively toward the plurality of reaction mixtures and analyzing results therefrom, at a speed on an order of one reaction per second, by comparing the compositions contained within the plurality of reaction vessels to a target composition, the target composition is the single target end product or an intermediate of the single target end product;
 an automation subsystem configured and arranged to:
  seal the plurality of reaction vessels;
  selectively move the plurality of reaction vessels to and from the at least one reactor module for the different periods of time based on the experimental design parameters; and
  unseal the plurality of reaction vessels and selectively move the reaction mixtures proximal to the analysis subsystem; and
 control circuitry configured and arranged to provide the experimental design parameters to the automation subsystem for controlling the reactions within the plurality of reaction vessels and to identify optimum reaction conditions for synthetically forming the single target end product based on the analysis of the compositions received from the analysis subsystem, the optimum reaction conditions including a set of reaction conditions to synthetically form the single target end product as optimized for an objective, the set of reaction conditions including select values for each of the plurality of reaction conditions as defined by the experimental design parameters.

19. The apparatus of claim 18, wherein the automation subsystem further includes a movable arm and a distribution chamber configured and arranged to contain a plurality of caps for the plurality of reaction vessels, wherein the movable arm and distribution chamber are configured and arranged to distribute the plurality of caps for the plurality of reaction vessels and to seal the plurality of reaction vessels using the distributed plurality of caps, the plurality of reaction vessels each being configured and arranged to contain between 5 microliters (µl) to 20 µl of liquid.

20. The apparatus of claim 18, further including a dispensing subsystem configured and arranged to deliver reagents to the plurality of reaction vessels for the plurality of reaction mixtures having the plurality of reaction conditions, wherein:
 the automation subsystem configured and arranged to selectively move the plurality of reaction vessels from a location proximal to the dispensing subsystem to the at least one reactor module; and
 the control circuitry configured and arranged to provide the experimental design parameters to the dispensing subsystem, the experimental design parameters including identification of reagents, concentration of reagents for each of the plurality of reaction vessels, and the plurality of reaction conditions.

* * * * *